United States Patent
Ikeda et al.

(10) Patent No.: US 7,054,406 B2
(45) Date of Patent: May 30, 2006

(54) X-RAY CT APPARATUS AND METHOD OF MEASURING CT VALUES

(75) Inventors: Yoshihiro Ikeda, Tochigi-ken (JP); Masahiro Ozaki, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 83 days.

(21) Appl. No.: 10/653,241

(22) Filed: Sep. 3, 2003

(65) Prior Publication Data
US 2004/0114706 A1    Jun. 17, 2004

(30) Foreign Application Priority Data
Sep. 5, 2002    (JP) .............................. 2002-259600

(51) Int. Cl.
*A61B 6/03* (2006.01)
*H05G 1/64* (2006.01)
(52) U.S. Cl. ................................. 378/8; 378/4; 378/98
(58) Field of Classification Search .................... 378/4, 378/8, 5, 19, 62, 901, 95, 114, 98; 382/131, 382/132
See application file for complete search history.

(56) References Cited

U.S. PATENT DOCUMENTS

| | | | | |
|---|---|---|---|---|
| 5,412,562 A | * | 5/1995 | Nambu et al. ................. | 378/10 |
| 5,459,769 A | | 10/1995 | Brown | |
| 5,612,985 A | | 3/1997 | Toki et al. | |
| 5,987,093 A | * | 11/1999 | Ozaki .......................... | 378/62 |
| 6,188,744 B1 | * | 2/2001 | Shinohara et al. ............. | 378/8 |
| 6,198,797 B1 | * | 3/2001 | Majima et al. ................ | 378/98 |
| 6,363,134 B1 | * | 3/2002 | Suzuki ......................... | 378/15 |
| 6,826,297 B1 | * | 11/2004 | Saito et al. ................... | 382/131 |
| 6,845,142 B1 | * | 1/2005 | Ohishi .......................... | 378/8 |
| 2002/0054038 A1 | * | 5/2002 | Nemoto ........................ | 345/419 |
| 2003/0097076 A1 | | 5/2003 | Nambu et al. | |

FOREIGN PATENT DOCUMENTS

JP   06-114049   4/1994
JP   2000-175900   6/2000

* cited by examiner

Primary Examiner—Edward J. Glick
Assistant Examiner—Irakli Kiknadze
(74) Attorney, Agent, or Firm—Oblon, Spivak, McClelland, Maier & Neustadt, P.C.

(57) ABSTRACT

An X-ray CT (computed tomography) apparatus is disclosed. The X-ray CT apparatus include an X-ray supply unit performing low-dose X-ray scans and high-dose X-ray scans for a patient in which a contrast medium has been injected. The collected X-ray projection data are reconstructed to generate image data for low-dose scans and high-dose scans. In the low-dose scans that precede the high-dose scans, plural images are obtained in succession, in which ROIs (regions of interest) are set in given positions. A CT value calculating unit calculates the CT values in the ROIs in succession, and the calculated CT values are displayed as a time-density curve (TDC). The operator observes the state in which the contrast medium flows into the ROIs, and determines the timing at which the high-dose X-ray scan is started.

9 Claims, 18 Drawing Sheets

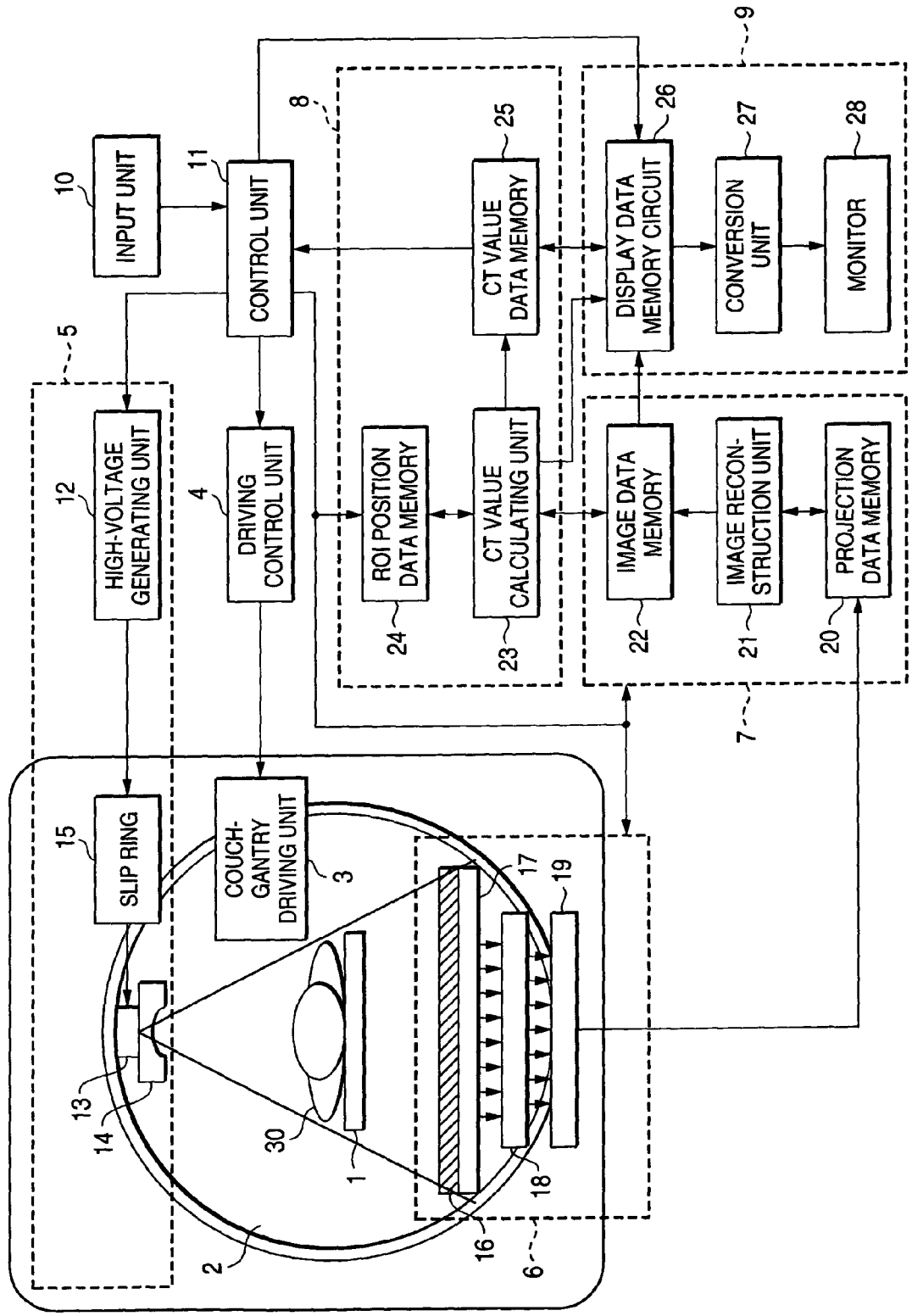

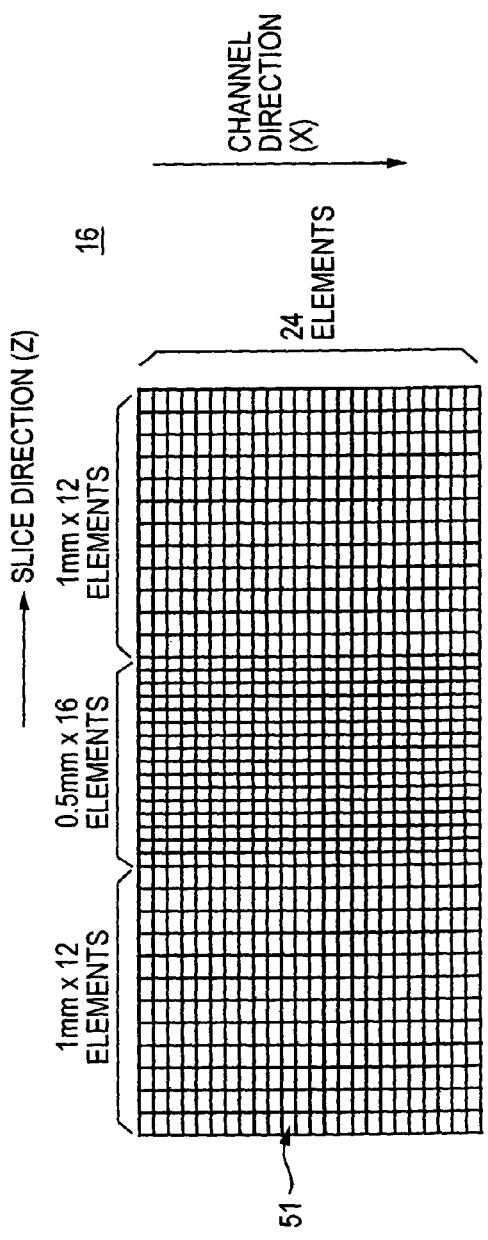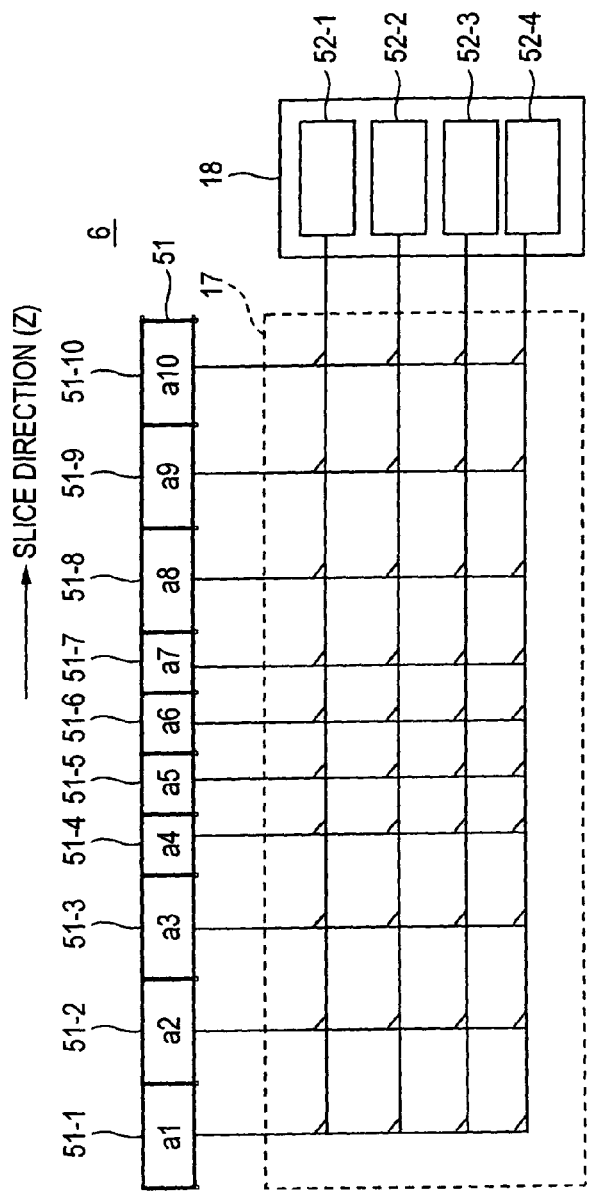
FIG. 2A
FIG. 2B

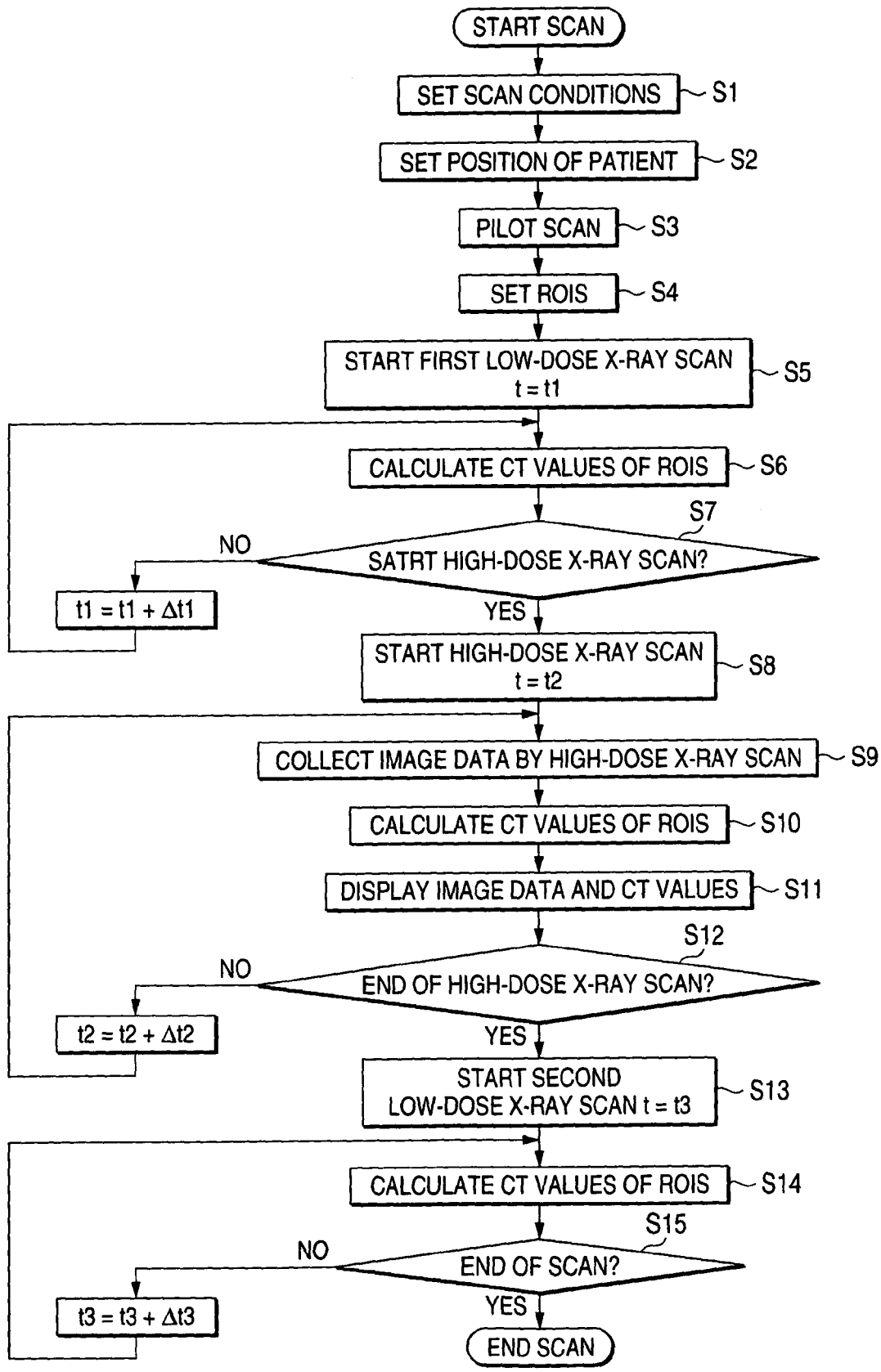

FIG. 4

|  | TUBE VOLTAGE | TUBE CURRENT | INTER-SCAN INTERVAL |
|---|---|---|---|
| FIRST LOW-DOSE X-RAY SCAN | 120kV | 50mA | 2 SECONDS |
| HIGH-DOSE X-RAY SCAN | 120kV | 100mA | 1 SECOND |
| SECOND LOW-DOSE X-RAY SCAN | 120kV | 70mA | 2 SECONDS |

X-RAY CT APPARATUS AND METHOD OF MEASURING CT VALUES

CROSS-REFERENCES TO RELATED APPLICATIONS

This application is based upon and claims the benefit of priority from prior Japanese Patent Application No. 2002-259600 filed on Sep. 5, 2002; the entire contents of which are incorporated herein by reference.

FIELD OF THE INVENTION

The present invention relates to an X-ray computer tomography (CT) apparatus and, more particularly, to an X-ray CT apparatus capable of observing CT values and a method of measuring CT values.

DESCRIPTION OF THE BACKGROUND

In a modern X-ray CT apparatus, X-ray detectors and arithmetic processors have been operated at higher speeds and enhanced in performance. With this trend, real-time display of X-ray CT images has been enabled by high-speed image reconstruction performed concurrently with collection of X-ray data.

Furthermore, dynamic computer tomography utilizing such high-speed tomographic technique has been developed and already put into practical use in clinical sites. The dynamic computer tomography includes consists of tomographically imaging slice positions plural times and observing changes of CT values with time in the images in a real-time. Especially, in contrast enhanced dynamic CT using a contrast medium, computational processing is performed on the basis of information indicating how CT values change with time, the CT values indicating the amount of the contrast medium flowing through a blood vessel. A parameter such as the flow rate of blood is calculated and visualized. Thus, the kinetics of blood circulation through the body is observed.

Contrast media used in contrast enhanced dynamic CT are classified into a type such as xenon-based contrast media that ooze out from blood capillaries and are accumulated in tissues in the human head and another type such as iodinated contrast media that do not ooze out from blood capillaries. Recently, the latter iodinated contrast media have been used.

In contrast enhanced dynamic CT using an iodinated contrast medium, the medium is first injected from an elbow vein, and then CT scanning is started after a lapse of a given time T1. After a lapse of a given time T2, the scanning is ended. This time T1 corresponds to the time required for the contrast medium injected in the elbow vein to reach the slice to be tomographically imaged. The time T2 corresponds to the time taken for the contrast medium to flow out (disappear) after entering the slice planes.

These times depend on the velocity of blood stream and therefore are different among patients. Consequently, taking account of the range of variations among patients, T1 is empirically set to the value in the shortest case. T2 is empirically set to the value in the longest case.

According to this method, a large margin is contained in the period from the beginning to the end of the CT scanning. There is the possibility that the X-ray dose to the patient is high.

A first method for solving this problem is to perform X-ray scanning at low-dose at slice positions to be diagnosed. If the contrast medium appears in the blood vessels in the CT images at the given slice positions obtained by the low-dose X-ray scanning, the scanning is switched to X-ray scanning using a high-dose. However, the timing of arrival cannot be easily known because signs or symptoms of arrival of the contrast medium cannot be known from the images.

On the other hand, in a second method described in Japanese Patent Publication (Kokai) No. 11-342125, a pilot image at the slice position is taken tomographically. A region of interest (hereinafter mentioned as the "ROI") is set in the area showing blood vessels of the pilot image data. Low-dose X-ray scanning is performed at this slice position. The CT value at the ROI of the image data is calculated. When this CT value exceeds a preset threshold value, the scanning is automatically switched to high-dose X-ray scanning.

In a third method described in Japanese Patent Publication (Kokai) No. 6-114049, the timing at which the CT value at a given ROI of image data obtained by low-dose X-ray scanning exceeds a first threshold value is automatically detected in the same way as the foregoing method. On the basis of the detected signal, high-dose X-ray scanning is started. Furthermore, the timing at which the CT value at the ROI on the images obtained by the high-dose X-ray scanning decreases below a second threshold value is similarly automatically detected. Thus, CT scanning is ended.

In the second and third methods described above, the apparatus compares the CT values of blood vessel regions with a preset threshold value. Thus, the timing at which high-dose X-ray scanning is started or ended is automatically set. In practice, however, it has been difficult to precisely judge the timing at which high-dose X-ray scanning is started or ended from the comparisons with the uniquely defined threshold values, because peak CT values and profiles of the time-density curve (hereinafter mentioned as the "TDC") of CT values are different among patients. Accordingly, it has been difficult to precisely judge the timing of irradiation in high-dose X-ray scanning (especially, the timing of the end of irradiation). There is the possibility that the patient receives a high-dose of X-rays in high-dose X-ray scanning.

SUMMARY OF THE INVENTION

It is an object of the present invention to provide an X-ray CT apparatus and CT value measuring method capable of collecting necessary information and minimizing X-ray dose.

To solve the foregoing problem, a first aspect of the present invention may comprise an X-ray source configured to irradiate X-rays onto an object to be examined, an X-ray detection unit configured to detect X-rays transmitted through the object, a driving unit configured to rotate at least one of the X-ray source and the X-ray detection unit around the object, an image data generation unit configured to generate image data on the basis of projection data using the X-ray detection unit, a ROI setting unit configured to set up a region of interest (ROI) in first image data from the image data generation unit, prior to injecting a contrast medium into the object, a CT value calculating unit configured to calculate computer tomography (CT) values in the region of interest being set in second image data from the image data generation unit, on the basis of positional information of the region of interest, the second image data being generated plural times after injecting the contrast medium into the object and a CT value display unit configured to display changes of CT values with time calculated by the CT value calculating unit.

A second aspect of the present invention may comprise an X-ray source configured to irradiate X-rays into an object to be examined, an X-ray detection unit configured to detect X-rays transmitted through the object, a driving unit configured to rotate at least one of the X-ray source and the X-ray detection unit around the object, an image data generation unit configured to generate image data on the basis of projection data using the X-ray detection unit, a ROI setting unit configured to set up a region of interest in first image data from the image data generation unit, prior to injecting a contrast medium into the object, a CT value calculating unit configured to calculate CT values in the region of interest being set in second image data from the image data generation unit, on the basis of positional information of the region of interest, the second image data being generated plural times, after injecting the contrast medium into the object, a threshold setting unit configured to set at least one threshold value for the CT values, a CT value comparing unit configured to keep comparing the CT values calculated by the CT value calculating unit with the threshold value set by the threshold setting unit and to generate a coincidence signal when both substantially agree and an irradiation condition setting unit configured to set conditions of the X-ray irradiation on the basis of an output signal from the CT value comparing unit.

A third aspect of the present invention may comprise an X-ray source configured to irradiate X-rays into an object to be examined, an X-ray detection unit configured to detect X-rays transmitted through the object, a moving unit configured to move the object in a given direction, an image data generation unit configured to generate image data on the basis of projection data from the object collected from the X-ray detection unit plural times, while moving the object by the moving unit, a ROI setting unit configured to set at least one region of interest in the image data which is obtained by the image data generation unit and a CT value calculating unit configured to calculate CT values in the region of interest being set in the image data which is obtained by the image data generation unit, while generating the image data by the image data generation unit.

A fourth aspect of the present invention may comprise an X-ray source configured to irradiate X-rays onto an object to be examined from plural directions, an X-ray detection unit configured to detect X-rays transmitted through the object, a driving unit configured to rotate at least one of the X-ray source and the X-ray detection unit around the object, a moving unit configured to move the object in a given direction, an image data generation unit configured to generate image data on the basis of projection data from the object collected from the X-ray detection unit plural times while moving the object by the moving unit, an ROI setting unit configured to set a region of interest in the image data generated by the image data generation unit, a CT value calculating unit configured to calculate CT values, in pixels, in the region of interest of the image data, while generating the image data by the image data generation unit, a range setting unit configured to set a range of the CT values, a pixel number measuring unit configured to measure the number of pixels providing CT values which are calculated by the CT value calculating unit and which are contained within the range set by the range setting unit, a threshold setting unit configured to set a threshold value for the number of pixels and a pixel number comparing unit configured to keep comparing the number of pixels obtained by the pixel number measuring unit with the threshold value of the number of pixels set by the threshold setting unit and to generate an instruction signal for stopping X-ray irradiation when both substantially agree.

A fifth aspect of the present invention may comprise generating first image data which is obtained by an X-ray detection unit with respect to a position of a object to be examined, prior to injecting a contrast medium into the object, setting a region of interest in the first image data for calculating CT values, generating second image data which is obtained by the X-ray detection unit plural times after injecting the contrast medium into the object, calculating CT values in the region of interest being set in the second image data on the basis of positional information of the region of interest set by the setting step, while generating second image data and displaying changes of the CT values with time which is obtained by the calculation.

A sixth aspect of the present invention may comprise setting a region of interest for image data, generating image data on the basis of projection data collected by using an X-ray source and an X-ray detection unit around a object to be examined plural times, while moving the object in a given direction by a moving unit, calculating CT values in the region of interest being set in the image data on the basis of positional information of the region of interest set by the setting step, while generating the image data, and ending scanning on the basis of the calculated CT values.

In accordance with the aspect of the present invention, the optimum timing at which CT scanning is started or ended can be determined easily. Therefore, an exact amount of image data necessary for diagnosis is collected. Consequently, wasteful X-ray dose to the patient can be reduced.

BRIEF DESCRIPTION OF THE DRAWINGS

Other objects and features of the invention will become apparent to those skilled in the art as the disclosure is made in the following description of embodiments of the invention as illustrated in the accompanying sheets of drawings.

FIG. 1 is a block diagram showing the construction of an X-ray CT apparatus according to a first embodiment of the present invention;

FIG. 2 is a diagram illustrating an array of X-ray detecting elements and "data bunching" in the first embodiment;

FIG. 3 is a flow chart illustrating a procedure in which contrast enhanced dynamic CT images are taken in the first embodiment;

FIG. 4 is a diagram illustrating conditions of X-ray irradiation and data collection in low-dose and high-dose X-ray scans in the first embodiment;

DETAILED DESCRIPTION OF THE INVENTION

Figure 5:
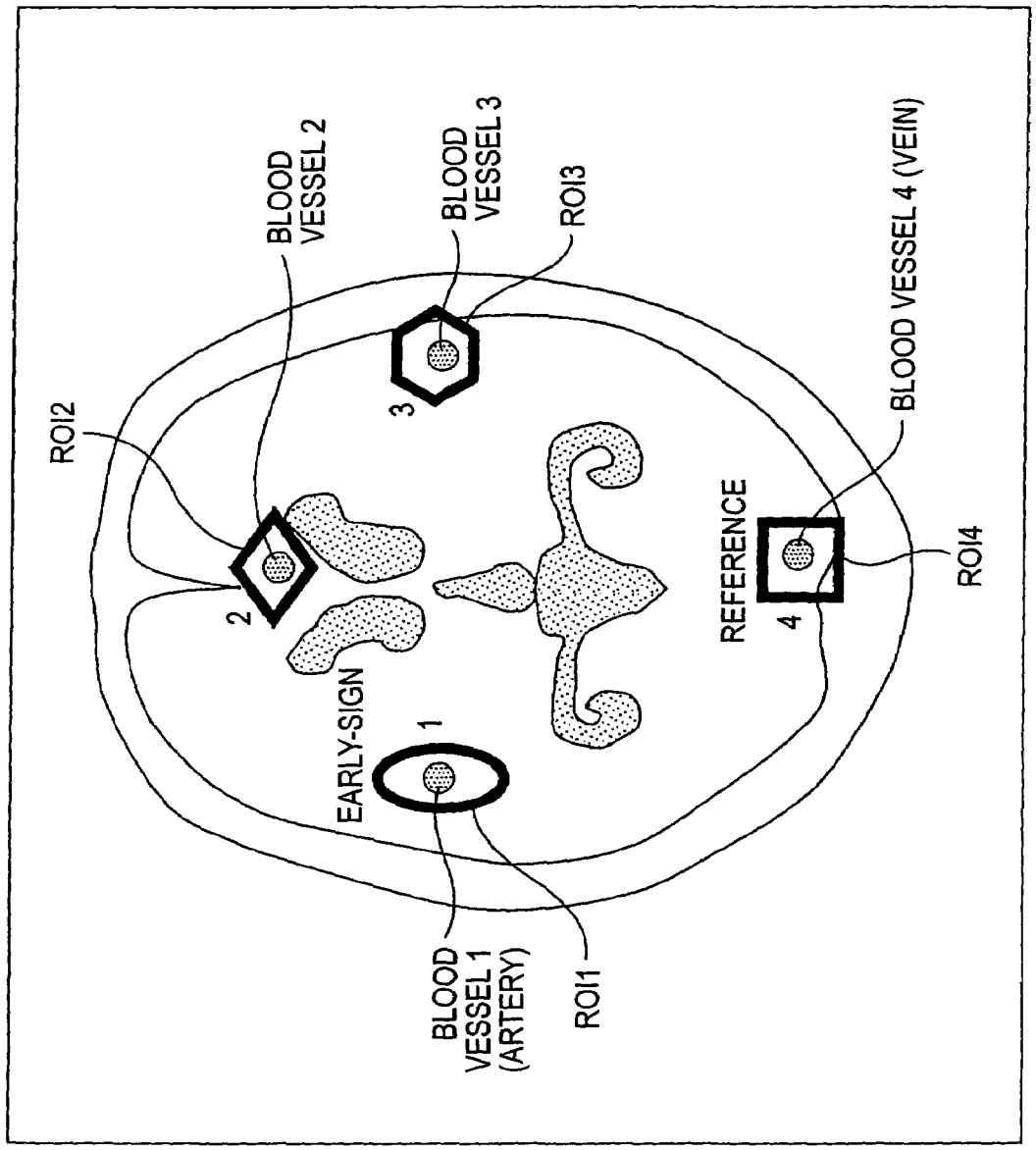
FIG. 5 is a diagram illustrating a method of setting ROIs for measurement of CT values in the first embodiment.

A first embodiment in accordance with the present invention will be explained with reference to FIGS. 1 to 7.

In the present embodiment, the timing at which high-dose X-ray scanning is started and the timing at which the scanning is ended are determined in contrast enhanced dynamic CT. In order to determine the timings, the CT values of image data are calculated by first low-dose X-ray scanning (first scanning), high-dose X-ray scanning (second scanning), and second low-dose X-ray scanning (third scanning). The CT values obtained by the first to third scanning are displayed as a TDC (time-density curve) in a real-time.

FIG. 1 is a block diagram schematically showing the whole structure of an X-ray CT apparatus according to the present embodiment. This CT apparatus has a couch 1 on which an object, for example, a patient 30 to be examined is placed, a rotating portion of gantry 2, and a couch-gantry driving unit 3 for translating and rotating the couch 1 and rotating portion of gantry 2. This gantry has an opening through which the patient 30 and a top plate (described later) for placing the patient 30 thereon are inserted. The rotating portion of gantry 2 rotates around the patient 30. The apparatus further includes a driving control unit 4 for controlling the couch-gantry driving unit 3, an X-ray supply unit 5 for irradiating X-rays at the patient 30, and a projection data acquisition unit 6 for collecting X-ray data transmitted through the patient 30.

This X-ray CT apparatus further includes a reconstruction unit 7 for generating CT image data by reconstructing the X-ray projection data collected by the projection data acquisition unit 6 and a CT value evaluating unit 8 for calculating the CT values from the image data. In addition, the apparatus has a monitoring unit 9 for providing a time series display of the CT image and CT values, an input unit 10 for entering scan conditions, and a control unit 11 providing an overall control of all of these units.

The couch 1 has the top plate that can be slid in its longitudinal direction by driving of the couch-gantry driving unit 3. The patient 30 is normally so placed that the direction of the body axis is substantially coincident with the longitudinal direction of the top plate.

The driving control unit 4 controls movement of the couch 1 in the longitudinal direction of the top plate or rotation of the rotating portion of gantry 2 according to a control signal from the control unit 11.

On the other hand, the X-ray supply unit 5 has an X-ray tube 13 for irradiating X-rays into the patient 30, a high-voltage generating unit 12 for generating a high voltage applied between the anode and cathode of the X-ray tube 13, an X-ray collimator 14 for collimating the X-rays projected from the X-ray tube 13, and a slip ring 15 for supplying electric power to the X-ray tube 13 mounted in the rotating portion of gantry 2.

The X-ray tube 13 is a vacuum tube that produces X-rays by accelerating electrons by means of a high voltage supplied from the high-voltage generating unit 12 and impinging the electrons against a tungsten target. The X-ray collimator 14 is positioned between the X-ray tube 13 and the patient 30 and has functions to collimate the X-ray beam radiated from the X-ray tube 13 down to a given image size, thus producing a clear image.

The X-ray collimator 14 shapes the X-rays radiated from the X-ray tube 13 into X-rays like a conic (pyramidal) beam or fan beam corresponding to an effective field of view (FOV).

The rotating portion of gantry 2 has the X-ray tube 13 in the X-ray supply unit 5, and an X-ray detector 16, a switching matrix 17, a data acquisition system (hereinafter abbreviated as the "DAS") 18, the sending portion of a non-contacting data transmission unit 19 in the projection data acquisition unit 6, and the slip ring 15. The X-ray detector 16, projection data acquisition unit 6, switching matrix 17, DAS 18, and sending portion are disposed on the opposite side of the patient 30 inserted in the opening in the rotating portion of gantry 2 from the X-ray tube 13.

The X-ray tube 13 and X-ray detector 16 are mounted on the rotating portion of gantry 2 which may rotate relative to the stationary portion of the gantry. The X-ray tube 13 and X-ray detector 16 are rotated at a high speed of 1 to 2 turns per second around a center axis of rotation parallel to the direction of body axis of the patient 30 according to a driving control signal from the driving control unit 4.

The projection data acquisition unit 6 has the X-ray detector 16 for detecting X-rays transmitted through the patient 30, the switching matrix 17 for bunching signals from the X-ray detector 16 into a given number of channels, the DAS 18, and a data transmission unit 19. The X-ray detector 16 has a plurality of detecting elements each consisting of a scintillator and a photodiode.

An array of the X-ray detecting elements in the X-ray detector 16 is described using FIG. 2A. FIG. 2A is an expanded view of the X-ray detector 16. In the multi-slice X-ray detector 16, forty (40), for example, X-ray detecting elements 51 are arranged in the slice direction (Z-direction) that is the direction of body axis of the patient 30, and twenty-four (24) X-ray detecting elements 51 are arranged in the channel direction (X-direction) perpendicular to the slice direction. In practice, however, the X-ray detecting elements 51 arranged in the channel direction are mounted on the rotating portion of gantry 2 along an arc that centers at the focal point of the X-ray tube 13. In the slice direction of the X-ray detector 16, sixteen X-ray detecting elements 51 are arranged in the array center to obtain data about slices each 0.5 mm thick. Twelve (12) X-ray detecting elements 51 for obtaining data about slices each 1.0 mm thick are arranged at each of the opposite ends of the 16 X-ray detecting elements 51.

Referring back to FIG. 1, the switching matrix 17 of the projection data acquisition unit 6 bunches signals received from the X-ray detecting elements in the slice direction, into a given number of channels and supplies them to the DAS 18 when the signals detected by the X-ray detector 16 are routed to the DAS 18.

The DAS 18 has plural channels of receiving portion which convert current signals from the X-ray detector 16 into voltages. These voltages are converted into digital signals by A/D converters (not shown) to thereby generate projection data.

The data transmission unit 19 sends the projection data delivered from the DAS 18 to a projection data memory 20 (described later) in the reconstruction unit 7 by optical transmission means, for example. This method of data transmission can be replaced by other method as long as signal transmission between the rotator and stationary part is possible. For instance, the slip ring 15 already described may be used. However, a huge amount of two-dimensional projection data is detected in the X-ray detector 16 during one rotation (for about 1 second). To transmit such a huge amount of projection data, the DAS 18 and data transmission unit 19 are required to have a high-speed processing function.

"Data bundling" in the projection data acquisition unit 6 will be described using FIG. 2B. In this FIG. 2B, for simplicity of illustration, a case where 10 X-ray detecting elements 51-1 to 51-10, are arranged in the slice direction in one channel lying in the channel direction is described.

In the X-ray detector 16 of FIG. 2B, four X-ray detecting elements 51-4 to 51-7, are arranged at an interval of 1 mm, for example, in the center in the slice direction. Three X-ray detecting elements, 51-1 to 51-3, and three elements, 51-8 to 51-10, are arranged at an interval of 2 mm at the both ends. On the other hand, the DAS 18 is composed of four receiving portions 52-1 to 52-4, for example. The switching matrix 17 bundles data consist of 10 rows of signals, for example, detected by the X-ray detecting elements into 4 rows, for example.

By means of this "data bundling", the slice thickness of the multiple slices can be varied. For example, by connecting the X-ray detecting elements 51-4 to 51-7 to the receiving portions 52-1 to 52-4, respectively, of the DAS 18 via the switching matrix 17, data of 4 slices each having a slice width of 1 mm is obtained. On the other hand, when data of 4 slices each having a slice width of 2 mm is required the X-ray detecting element 51-3 is connected with the receiving portion 52-1. The X-ray detecting elements 51-4 and 51-5 are connected with the receiving portion 52-2. The X-ray detecting elements 51-6 and 51-7 are connected with the receiving portion 52-3. Furthermore, the X-ray detecting element 51-8 is connected with the receiving portion 52-4.

By means of the "data bundling" described so far, the apparatus can cope with a case where a narrow region is tomographically imaged at a high resolution and also with a case where a wide area is tomographically imaged at a high sensitivity.

Referring back to FIG. 1, the reconstruction unit 7 has the projection data memory 20, an image reconstruction unit 21, and an image data memory 22.

The projection data memory 20 is a memory for storing projection data about the patient 30, the data being sent via the data transmission unit 19 after detection by the X-ray detector 16. The image data memory 22 is a memory for storing image data generated by reconstructing the projection data. In the present embodiment, X-ray projection data collected to generate pilot image data for setting the ROIs for calculating CT values, high-dose X-ray scan image data for clinical diagnosis, first low-dose X-ray scan image data for detecting the timing at which the high-dose X-ray scanning is started and second low-dose X-ray scan image data for detecting the timing at which the scanning is ended, are stored in the projection data memory 20. Also, various kinds of image data obtained by reconstructing the above-described projection data are stored in the image data memory 22.

The image reconstructing unit 21 reconstructs the projection data stored in the projection data memory 20 and generates image data about pilot images, first low-dose X-ray scan images, high-dose X-ray scan images, and second low-dose X-ray scan images.

The CT value evaluating unit 8 has an ROI position data memory 24, a CT value calculating unit 23, and a CT value data memory 25.

In the ROI position data memory 24, information about the position of the ROI set at a given position in the pilot image data by the mouse (described later) of the input unit 10 is stored. Where the first low-dose or high-dose X-ray scanning reveals that the setting of this ROI is not appropriate, the operator manipulates the mouse or keyboard, thus varying the ROI. Concomitantly, the positional information is updated.

The CT value calculating unit 23 calculates the CT values of the first low-dose X-ray scan image data, high-dose X-ray scan image data, and second low-dose X-ray scan image data on the basis of the information about the positions of the ROIs stored in the ROI position data memory 24, and stores the results of the calculations in the CT value data memory 25.

The monitoring unit 9 has a display data memory 26, a conversion unit 27, and a monitor 28. The display data memory 26 has an image data storage area for storing image data to be displayed on the monitor 28 and a TDC data storage area for storing graphs such as TDCs, numerical values such as CT values, and alphanumerical data. The newest image data is stored in the image data storage area and updated in succession. CT values obtained from image data from the first low-dose X-ray scanning, high-dose X-ray scanning, or second low-dose X-ray scanning are stored in the TDC data storage area. These kinds of data for display on the monitor 28 are D/A converted by the conversion unit 27 and converted into a TV format. Then, the data are displayed on the monitor 28. The operator can interactively communicate with the apparatus using the monitor 28 of the monitoring unit 9 and the input unit 10.

The input unit 10 is an interactive interface fitted with a display panel and input devices such as a keyboard, various switches, and a mouse. Prior to CT scanning, the operator sets various scan conditions via the input unit 10. In the stage when pilot image data is selected, the operator sets ROIs on this image for calculations of CT values. If any one of these ROI positions is found to be inappropriate during the first low-dose X-ray scanning or high-dose X-ray scanning, the ROI can be modified or a new setting can be made by a similar procedure.

The control unit 11 has a CPU and a memory (none of which are shown). Various scan conditions and various command signals sent from the input unit 10 are stored in the internal memory. According to instructions from the input unit 10, the control unit 11 provides an overall control of the various units in the system such as the driving control unit 4, X-ray supply unit 5, projection data acquisition unit 6, reconstruction unit 7, CT value evaluating unit 8, and monitoring unit 9. Concurrently with the execution of the scanning, the system performs reconstruction processing and calculations of CT values and displays the results. These operations are repeated and thus image data and TDC data are displayed in a real-time.

A procedure in which contrast enhanced dynamic CT images are taken in the first embodiment of the present invention is described using FIGS. 1–7. FIG. 3 is a flow chart illustrating the procedure for taking the CT images in the present embodiment.

The apparatus operator enters various scan conditions from the input unit 10 prior to capture of X-ray CT images. Thus, the control unit 11 stores the scan conditions in a memory (not shown) (step S1). The scan conditions set at this stage include the collection condition of X-ray projection data, reconstruction conditions, and image display/record conditions.

The collection conditions of X-ray projection data include scanned region, scanning type, inter-slice spacing, the number of slices, tube voltage/tube current, scanned area size, inter-scan interval, view interval, and moving speed of the couch 1. Especially, the tube current and inter-scan interval is important parameters in reducing the X-ray dose in the present embodiment.

The collection conditions of X-ray projection data in the low-dose X-ray scanning and the high-dose X-ray scanning are set, for example, to values as shown in FIG. 4. That is, the tube current is 50 mA, and the inter-scan interval is 2 seconds in the first low-dose X-ray scanning. The tube current is 100 mA, and the inter-scan interval is 1 second in the high-dose X-ray scanning. The tube current is 70 mA and the inter-scan interval is 2 seconds in the second low-dose X-ray scanning. Note that any one of the tube current and the inter-scan interval shown in this figure may be selected. The inter-scan interval is the time interval between scans in taking plural images of data at a given slice position. For example, where the inter-scan interval is 2 seconds, and the rotational speed of the X-ray tube 13 and X-ray detector 16 is 1 turn/sec, 1 image is taken every two rotations. The view interval is the interval at which data is collected in the direction of rotation of the X-ray tube 13 and X-ray detector 16.

On the other hand, the reconstruction conditions include reconstruction method, reconstruction area size, and reconstruction matrix size. The image display conditions and record conditions include CT image display format and TDC display format.

After the setting of the various conditions described above, the patient 30 is placed on the top plate of the couch 1. This top plate and patient 30 are moved in the direction of the body axis such that the part of the patient 30 to be observed lies at a given location in the opening in the gantry (step S2) Then, pilot images are taken. Pilot image data is image data taken in advance to determine the positions of the slices tomographically taken relative to the diagnosed region of the patient 30. In the present embodiment, the ROIs for calculations of CT values are set using these images. With respect to the scanning type, the type set in step S1 is used. In this embodiment, a multi-slice system where the slice thickness is 2 mm and the number of slices is 4 is described.

In taking pilot image data, the operator enters instruction signals for moving the patient 30 and for rotation of the rotating portion of gantry from the input unit 10. The control unit 11 controls the couch-gantry driving unit 3 via the driving control unit 4 according to the instruction signals. Specifically, the couch-gantry driving unit 3 moves the patient 30 by a given distance in the direction of body axis. Then, the rotating portion of gantry 2 on which the X-ray tube 13 and the X-ray detector 16 are placed on the opposite sides of the patient 30 is rotated at a speed of at least one turn per second, and X-ray projection data about the patient 30 is collected.

The operation of the apparatus in generating X-ray CT image data is described below by taking capture of the pilot image data as an example. Image data generation in the first low-dose X-ray scanning, high-dose X-ray scanning, and second low-dose X-ray scanning (described later) is performed by similar procedures.

When the X-rays are irradiated into the patient 30, the high-voltage generating unit 12 supplies tube voltage and tube current to the X-ray tube 13 on the basis of the set conditions including the tube voltage and tube current. The X-ray tube 13 receiving the supply of this electric power irradiates a conical beam of X-rays or a fan beam of X-rays into the patient 30. When the pilot image data is taken, electric power corresponding to an X-ray dose similar to high-dose X-ray scanning is supplied to the X-ray tube 13. Furthermore, the inter-scan interval is set in the same way as in the high-dose X-ray scanning.

The X-rays radiated from the X-ray tube 13 are transmitted through the patient 30 and then detected by the X-ray detector 16 of the projection data acquisition unit 6. Specifically, the X-rays transmitted through the patient 30 are converted into electric charge proportional to the transmission dose by the X-ray detecting elements 51 in the X-ray detector 16. Of these elements 51, 16 elements are arrayed in the slice direction, and 912 elements are arrayed in the channel direction. The charge is then amplified and A/D converted by the receiving portions 52-1 to 52-4, in the DAS 18. Thus, X-ray projection data is created.

Subsequently, the X-ray projection data is sent to the data transmission unit 19. The electrical signal is converted into an optical signal in the sending portion of the data transmission unit 19 mounted on the rotating portion of gantry 2. This optical signal is received by the receiving portion of the data transmission unit 19 of the stationary portion of the gantry. These data are stored in the projection data memory 20 of the reconstruction unit 7. That is, the detecting operation is repeated, for example, at a frequency of 1,000 per rotation while the X-ray tube 13 and X-ray detector 16 are continuously rotating around the patient 30. The projection data obtained at this time is stored in the projection data memory 20 via the switching matrix 17, DAS 18, and data transmission unit 19.

If X-ray projection data at the four slice positions each set, for example, to a slice thickness of 2 mm is stored in the projection data memory 20, the image reconstructing unit 21 reads out the projection data about the four slices which have been obtained from within a range, for example, of 180 degrees+the fan beam angle, performs reconstruction processing, and generates data about four images. The obtained image data are stored in the image data memory 22.

The CPU (not shown) of the control unit 11 stores the image data about four slices in the display data memory 26. Then, the conversion unit 27 performs a D/A conversion and a TV format conversion. The data are displayed on the monitor 28.

Then, the operator takes plural image data about different slice positions by the procedure described above, while moving the patient 30 in the direction of body axis in increments equal to the preset slice intervals (e.g., 1 mm interval). The operator selects the best slice position from the plural image data adapted for a contrast enhanced dynamic CT scan (described later) (step S3).

Then, the operator sets the ROIs for calculations of CT values regarding pilot image data at the optimum slice positions. The operator displays the pilot image data on the monitor 28 of the monitoring unit 9, and sets plural ROIs on the image using the mouse or keyboard of the input unit 10.

FIG. 5 is a view illustrating setting of ROIs on a pilot image of a human head. In this case, the operator sets the plural ROIs (ROI 1 to ROI 4) about blood vessels (blood vessels 1 to 4) displayed in the pilot image and attaches identification numbers 1 to 4 to them. It is especially preferable to display blood vessels 1 and 4 in a distinguished manner from the other ROIs. Where the contrast medium reaches the blood vessel 1 earliest, and reaches the blood vessel 4 latest. For example, characters such as "early-sign" and "reference" are placed as indexes near ROIs for the former and latter, respectively. Where the identification numbers or indexes hinder observation of the image, discriminations may be made by a shape of the boundary lines between the ROIs, line type, or colors as shown in FIG. 5. The shape of a ROI can be changed by dragging the boundary line with the mouse. Information about the ROI set by the mouse of the input unit 10 is stored in the ROI position data memory 24 via the control unit 11 (step S4).

After the end of the setting of the ROIs in the pilot image data for calculations of CT values, the operator injects an iodinated contrast medium into an elbow vein of the patient 30. After a lapse of a given time T0, the operator enters a command signal for starting the first low-dose scanning from the input unit 10 (step S5). The command signal is sent to the control unit 11. According to display conditions already stored in the control unit 11, the area in which TDC data and image data is stored are set in the display data memory 26. On the other hand, the control unit 11 receiving the command for starting the first low-dose X-ray scanning from the input unit 10 sends the collection conditions of the projection data for the first low-dose X-ray scanning to the projection data acquisition unit 6, sends the reconstruction conditions to the reconstruction unit 7, and controls them. The control unit 11 sends a control signal to the high-voltage generating unit 12 to perform the first low-dose X-ray scanning. The high-voltage generating unit 12 supplies tube voltage and tube current corresponding to the low-dose X-ray irradiation to the X-ray tube 13.

The X-rays radiated from the X-ray tube 13 are transmitted through the patient 30 and then detected by the projection data acquisition unit 6. Projection data at the four slice positions are created. The projection data which are at the optimum slice positions are selected from the projection data at these four slice positions as described above, sent to the receiving portion of the data transmission unit 19 in the stationary portion of the gantry from the sending portion of the data transmission unit 19 in the rotating portion of gantry 2, and stored in the projection data memory 20 of the reconstruction unit 7. The detection operation described above is performed from plural directions by rotating the X-ray tube 13 and X-ray detector 16 relative to the patient 30. The projection data obtained at this time are stored in the projection data memory 20 via the switching matrix 17, DAS 18, and data transmission unit 19.

When X-ray projection data about one image is stored in the projection data memory 20, the image reconstructing unit 21 reads out this X-ray projection data, reconstructs it, and stores the obtained image data in the image data memory 22. On the other hand, the CPU (not shown) of the control unit 11 stores the image data in the display data memory 26 and then performs a D/A conversion and a TV format conversion in the conversion unit 27. The results are shown on the monitor 28.

Then, the CPU of the CT value calculating unit 23 reads out the image data stored in the image data memory 22. ROIs are set in the image data on the basis of the positional information about the ROIs already stored in the ROI position data memory 24. The CT values in the ROIs are calculated. Where each ROI is made up of plural image pixels, the maximum value of the CT values obtained from each pixel is extracted and stored as a representative CT value in the CT value data memory 25. Instead of the maximum value, the average value may be taken as a representative CT value.

A CT value is the X-ray absorption coefficient of a material under calculation and expressed relative to a reference material. CT value=$K[(\mu-\mu_0)/\mu_0]$, where $\mu$ is the X-ray absorption coefficient of the material under calculation, $\mu_0$ is the X-ray absorption coefficient of the reference material, and K is a constant. A constant K=1000 is generally so adjusted that the CT value of water is 0 and that the CT value of air is −1000. The X-ray absorption coefficient indicates the ratio of X-ray absorption per unit thickness.

The display data memory 26 receives a control signal regarding display conditions from the control unit 11 and stores the first image data obtained by the first low-dose X-ray scanning instead of the pilot image data already stored in the image data storage area. At this time, supplemental information about the positions and shapes of the ROIs displayed in the pilot image data are stored intact in the same image data storage area. Furthermore, CT values obtained from the first image data of the first low-dose X-ray scanning are stored in the same TDC data storage area of the display data memory 26.

In this way, the first image data by the first low-dose X-ray scanning and plural ROI boundary lines are stored in the image data storage area of the display data memory 26. The plural CT values in the first image data obtained by the first low-dose X-ray scanning are stored differently for different ROIs in the TDC data storage area. These data are displayed on the monitor 28 in a real-time (step S6).

After a lapse of a given time (inter-scan interval $\Delta t1$), the second image data is obtained by the second low-dose X-ray scanning. The control unit 11 sends the next control signal to the high-voltage generating unit 12. The high-voltage generating unit 12 supplies tube voltage and tube current corresponding to a low X-ray dose to the X-ray tube 13. The X-ray tube 13 that is supplied with electric power irradiates X-rays into the patient 30. The projection data acquisition unit 6 collects projection data at the optimum slice positions in the patient 30. Similarly, the projection data acquisition unit 6 collects projection data from plural directions relative to the patient 30 while the rotating portion of gantry 2 rotates once at a high speed. The reconstruction unit 7 generates the second image data using these projection data by the first low-dose X-ray scanning and stores them in the image data memory 22.

The CPU of the CT value calculating unit 23 reads out the second image data which has been obtained by the first low-dose X-ray scanning and is stored in the image data memory 22. Then, the CPU sets ROIs for the second image data on the basis of the positional information about the ROIs stored in the ROI position data memory 24. The CT values in these ROIs are calculated, and the results are stored differently for different ROIs in the CT value data memory 25.

Then, the control unit 11 updates the first image data which has been obtained by the first low-dose X-ray scanning and already stored in the display data memory 26 to the newly obtained second image data obtained by the first low-dose X-ray scanning, and adds the ROI boundary lines to this image data. The CT values in the second image data and calculated by the CT value calculating unit 23 are also sent to the TDC data storage area of the display data memory 26 and stored adjacent to the previously stored CT values in the first image data.

Therefore, the monitor 28 provides a second image data and the TDC data of the CT values differently for different ROIs. The plural ROIs are attached to the second image data have been obtained by the first low-dose X-ray scanning. The CT values have been calculated in the first and second image data of the first low-dose X-ray scanning.

Generation of the third and subsequent image data by the first low-dose X-ray scanning at the optimum slice positions and calculation and display of CT values are similarly performed in succession at an inter-scan interval of $\Delta t1$. The obtained image data are stored in the image data memory 22 and the newest image data to which ROIs are attached are displayed on the monitor 28.

The CT value calculating unit 23 also calculates the CT values within ROIs for the first low-dose X-ray scan image data stored in the image data memory 22. The calculated CT values are stored in the CT value data memory 25. A time series display of the CT values is provided at the TDC on the monitor 28. In this case, the identification number of an ROI corresponding to each TDC and information such as an index are attached to each TDC.

Figure 6:
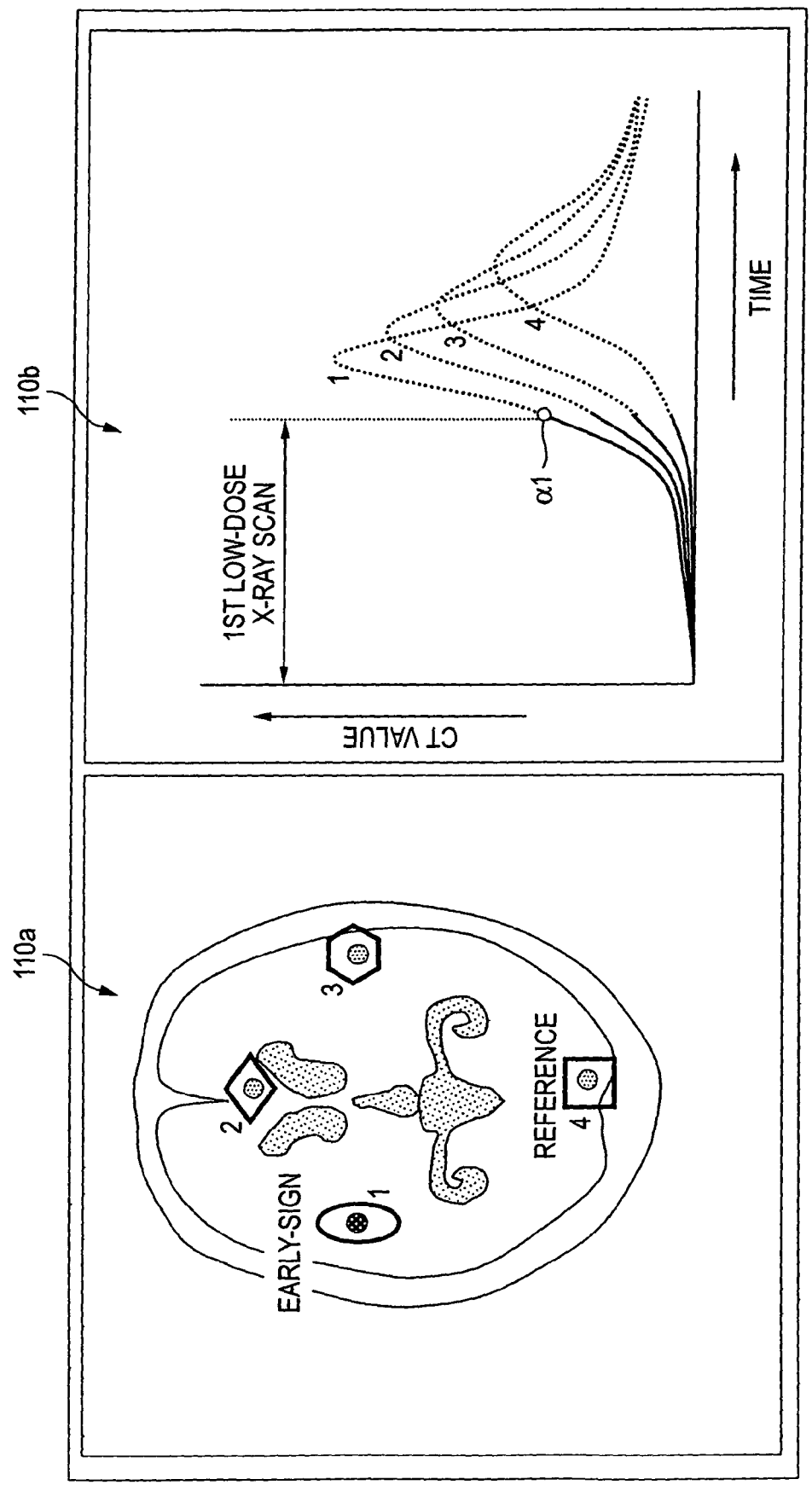
FIG. 6 is a diagram illustrating the TDCs at the end of first low-dose X-ray scanning in the first embodiment.

FIG. 6 shows the TDCs at the end of the first low-dose X-ray scanning. A CT image 110a of the human head in the first low-dose X-ray scanning and a TDC graph 110b of CT values are displayed on the monitor 28. In the TDC graph 110b, the solid-line indicates TDCs obtained by the first low-dose X-ray scanning. The broken-line indicate TDCs obtained by high-dose X-ray scanning and second low-dose X-ray scanning (described later).

In the initial-phase, first low-dose X-ray scanning, data about plural image data may be often collected before the contrast medium reaches the ROIs. In this case, the values of pixels in data about the plural images are preferably summed up and their average is taken. This is stored or displayed as data about one image. This method reduces the number of images. Furthermore, image data with high S/N can be obtained.

Then, the operator observes the TDCs of the ROIs displayed on the monitor 28 and estimates the timing of arrival of the contrast medium. For example, a special attention is paid to TDC ($\alpha 1$ of TDC graph 110b) in ROI tagged with "early-sign" meaning that the contrast medium arrives earliest within the slice plane of this CT image. The timing of the start of high-dose X-ray scanning is determined from the newest CT value and information including the shape (gradient) of the curve (step S7)

If the operator recognizes the optimum timing of start of the high-dose X-ray scanning, from the information about the TDCs, the operator enters a command signal for starting the high-dose X-ray scanning from the input unit 10 (step S8). The control unit 11 receives this command signal and sends a control signal for the high-dose X-ray scanning to the high-voltage generating unit 12. The high-voltage generating unit 12 supplies increased tube voltage and tube current to the X-ray tube 13 to perform an X-ray irradiation for the high-dose X-ray scanning.

In this high-dose X-ray scanning, the slice thickness of the multiple slices may be reduced (for example, to 1 mm) to improve the resolution in the slice direction. At this time, deterioration of the X-ray detecting sensitivity due to the decrease in the width of the X-ray detecting elements 51 may be compensated by an increase in the tube current.

The X-ray tube 13 receives the supply of the electric power for X-ray irradiation from the high-voltage generating unit 12 and changes the X-rays irradiates from a low X-ray dose for the first low-dose X-ray scanning to a high X-ray dose for the high-dose X-ray scanning. The projection data acquisition unit 6 collects X-ray projection data about four slices in the same way as the first low-dose X-ray scanning. That is, the projection data acquisition unit 6 collects the X-ray projection data obtained from plural directions about four slices while rotating the rotating portion of gantry 2 at a high speed. The reconstruction unit 7 generates the first image data using these projection data and stores the data in the image data memory 22 (step S9)

The CT value calculating unit 23 selects image data at the optimum slice positions from the first image data for the high-dose X-ray scanning, the first image data being stored in the image data memory 22. Then, the CT value calculating unit 23 calculates the CT values in the ROIs set in the selected image data on the basis of the positional information about the ROIs already stored in the ROI position data memory 24 and stores the CT values differently for the different ROIs in the CT value data memory 25 (step S10).

The control unit 11 updates the final image data obtained by the first low-dose X-ray scanning at the optimum slice positions already stored to the first image data obtained by the high-dose X-ray scanning in the image data storage area of the display data memory 26. ROI information previously set is attached to the high-dose X-ray scan image data intact and stored.

Furthermore, the control unit 11 supplies the CT values in the ROIs in the first image data obtained by the high-dose X-ray scanning to the TDC data storage area of the display data memory 26 and stores the CT values adjacent to the CT values obtained from the final image data derived by the first low-dose X-ray scanning. Accordingly, the first image data obtained by the high-dose X-ray scanning and stored in the display data memory 26 is displayed on the monitor 28 of the monitoring unit 9. In addition, TDCs of CT values in the plural image data by the first low-dose X-ray scanning and of CT values in the high-dose X-ray scanning are displayed differently for different ROIs (step S11).

After a lapse of an inter-scan interval of $\Delta t2$ since capture of the first image data by the high-dose X-ray scanning, the second image data is collected by the high-dose X-ray scanning in the same procedure as in the case of the first image data by the high-dose X-ray scanning, and is stored in the image data memory 22. Note that the inter-scan interval $\Delta t2$ at which image data is collected during the high-dose X-ray scanning and the inter-scan interval $\Delta t1$ at which image data is collected during the first low-dose X-ray scanning are scan conditions set by the operator prior to the scanning as mentioned previously. Preferably, they are so set that $\Delta t1 > \Delta t2$.

That is, in the high-dose scanning, the interval at which image data is collected is shortened compared with the first low-dose X-ray scanning, thus enhancing the time resolution of images. In contrast, the object of the first low-dose X ray scanning is to know the optimum timing at which the high-dose X-ray scanning is started in order to reduce the time required for high-dose X-ray scanning with a large dose to a minimum. Accordingly, in the first low-dose X-ray scanning that demands neither high image sensitivity nor high time resolution, the dose per X-ray irradiation is reduced. Furthermore, the inter-scan interval is prolonged, and the number of X-ray radiation per unit time is reduced. Inconsequence, the radiation dose per contrast enhanced dynamic CT scan is reduced.

Then, the control unit 11 updates the first scan image data obtained by the high-dose X-ray scanning and stored in the display data memory 26 to the second image data obtained by the high-dose X-ray scanning. On the other hand, the CPU of the CT value calculating unit 23 calculates the CT values in ROIs in the second image data stored in the image data memory 22. The CPU also stores the obtained CT values in the CT value data memory 25. Then, the control unit 11 sends the CT values to the TDC data storage area of the display data memory 26 and stores them together with the CT values of the first image data produced by the high-dose X-ray scanning and of the image data which were produced by the first low-dose X-ray scanning. The second image data produced by the high-dose X-ray scanning and stored in the display data memory 26 and TDC data about the CT values are displayed on the monitor 28.

Figure 7:
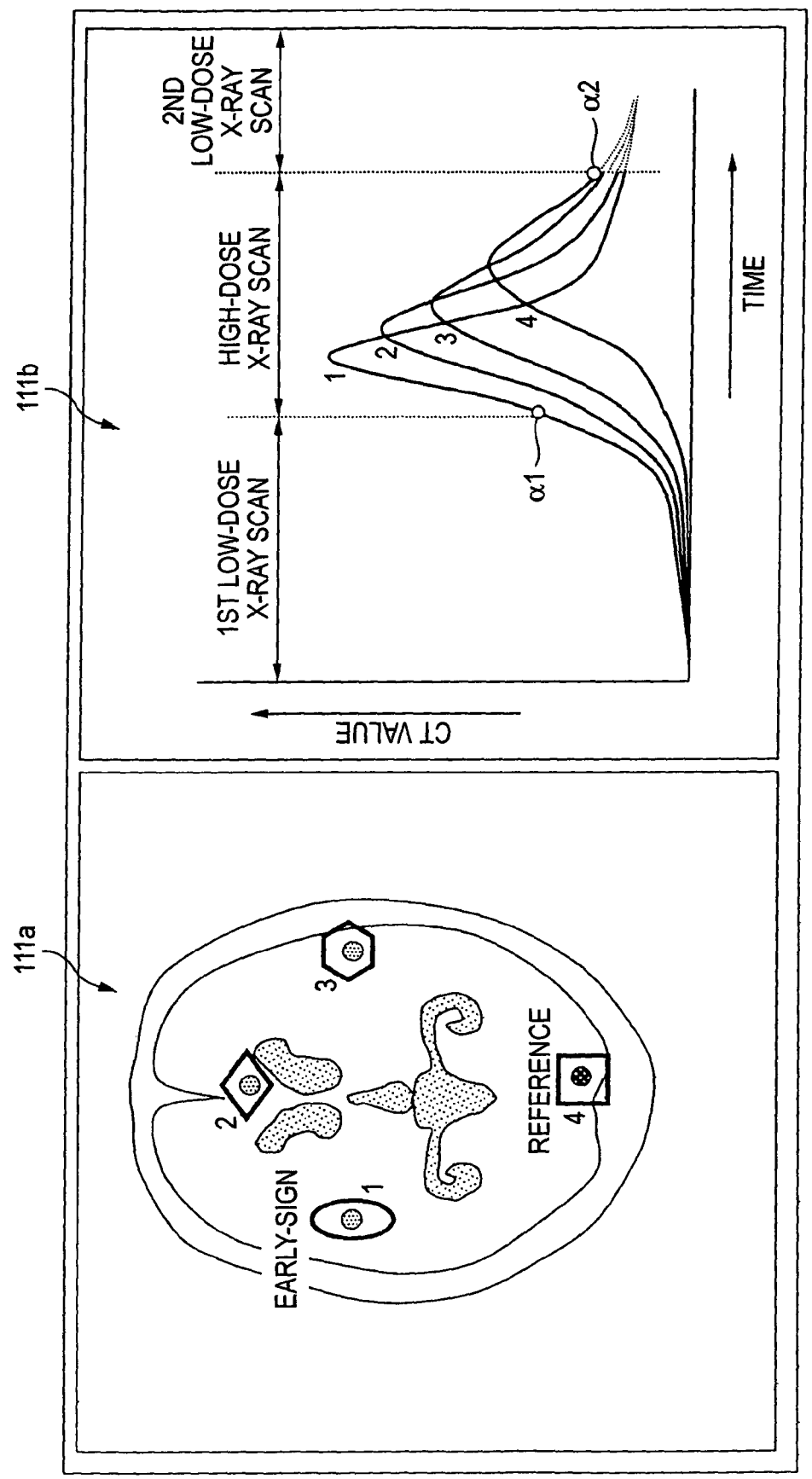
FIG. 7 is a diagram illustrating the TDCs at the end of high-dose X-ray scanning in the first embodiment.

Generation of third and subsequent image data by the high-dose X-ray scanning at the optimum slice positions and calculation of the CT values are continuously carried out similarly at an inter-scan interval of $\Delta t2$. The newest high-dose X-ray scan image data to which plural ROIs are attached as shown in FIG. 7 (described later) and TDC data about CT values obtained by the first low-dose X-ray scanning and by the high-dose X-ray scanning are displayed on the monitor 28.

In some cases, the positions of ROIs set in the pilot image data prior to injecting the contrast medium are not optimal. The operator observes the first low-dose X-ray scan image or high-dose X-ray scan image displayed on the monitor 28. If it is judged that the positions of the ROIs already set are not appropriate, the ROI positions are modified or new ROIs are set in the first low-dose X-ray scan image or high-dose X-ray scan image that is being displayed in a real-time, by a procedure similar to ROI setting performed in the pilot image data.

That is, the operator modifies ROIs or sets new ROIs about the first low-dose X-ray scan image or high-dose X-ray scan image displayed on the monitor 28, using the mouse or keyboard fitted to the input unit 10. For example, where the position and size of an ROI are modified by the keyboard, the ROI is selected with a key bearing the same number as the identification number of the ROI. Under this condition, the ROI is moved by an arrow key or otherwise enlarged or reduced with Page-up/Page-down key. At this time, the control unit 11 sends information about the ROI (positional information and information about the size and boundary line) sent from the mouse of the input unit 10 to the ROI position data memory 24, where the information is stored.

On the other hand, the CPU of the CT value calculating unit 23 successively reads out image data obtained by the first low-dose X-ray scanning and high-dose X-ray scanning and stored in the image data memory 22. Then, ROIs are set in the image data, on the basis of the positional information about the modified ROIs or newly set ROIs. The CT values of the ROIs are calculated and stored in the CT value data memory 25.

On the other hand, the control unit 11 stores the image data obtained by the first low-dose X-ray scanning or image data obtained by the high-dose X-ray scanning in the image data storage area of the display data memory 26. Also, the CT values in the updated ROIs or new ROIs described above are read from the CT value data memory 25, together with the CT values in the previously set ROIs, and stored in the TDC data storage area. Accordingly, with respect to the modified ROIs or new ROIs, TDCs about from the first image data obtained by the first low-dose X-ray scanning to the newest image data are displayed differently for different ROIs on the monitor 28. In this case, the modified and new ROIs and their TDCs are preferably displayed in a distinguished manner from the other ROIs.

As described so far, contrast enhanced dynamic CT image data with high-resolution are generated by the high-dose X-ray scanning. This image capture utilizing this high-dose X-ray scanning is continued until the contrast medium injected in the patient 30 is discharged by blood circulation through the body. It is important to know the optimum timing at which this capture is ended in order to reduce the radiation dose.

In the present embodiment, the method of determining the timing at which the high-dose X-ray scanning is ended is implemented by the operator in the same way as the determination of the timing at which the high-dose X-ray scanning is started. The apparatus offers useful information for the timing determination to the operator.

During high-dose X-ray scanning, the operator observes plural TDCs in ROIs displayed on the monitor 28, and estimates the timing at which the contrast medium is mostly discharged, from the TDC. Especially, an attention is paid to the TDC in the ROI with a tag "reference" meaning that the contrast medium disappears latest in the slice plane of the CT image. The timings are determined by making an overall judgment from the newest CT values or the shape of the TDCs (step S12).

FIG. 7 shows the TDCs at the end of high-dose X-ray scanning. A CT image 111a of the human head and a TDC graph 111b of CT values in high-dose X-ray scanning area displayed on the monitor 28. The solid-line of the TDC graph 111b are TDCs obtained by the first low-dose X-ray scanning and high-dose X-ray scanning. The broken-line indicates TDCs produced by the second low-dose X-ray scanning (described later).

The operator pays a special attention to the TDC ($\alpha 2$ of TDC graph 11b) in the ROI with a tag "reference" in that the contrast medium arrives latest within the slice plane of this CT image. If the operator determines the timing of the end of the present scanning from the newest CT value or the shape such as the gradient of the curve, the operator enters a command for starting second low-dose X-ray scanning from the input unit 10 (step S13)

The control unit 11 receives this command signal and sends a control signal for the second low-dose X-ray scanning to the high-voltage generating unit 12. This high-voltage generating unit 12 supplies tube voltage and tube current for performing second low-dose X-ray irradiation similar to the case of the first low-dose X-ray scanning to the X-ray tube 13. The X-ray tube 13 irradiates X-rays into the patient 30, the dose of the X-rays being varied from a dose adapted for the high-dose X-ray scanning to a lower dose adapted for the second low-dose X-ray scanning. The projection data acquisition unit 6 collects X-ray projection data from plural directions at the optimum slice positions of the patient 30 while rotating the rotating portion of gantry at a high speed. On the other hand, the reconstruction unit 7 generates image data for the second low-dose X-ray scanning using these projection data and stores the image data in the image data memory 22.

The CT value calculating unit 23 reads out the first image data which is obtained by the second low-dose X-ray scanning, and stored in the image data memory 22. The CT value calculating unit 23 the CT values in the ROI of the image data on the basis of the positional information about the plural ROIs stored in the ROI position data memory 24 and stores the CT values differently for different ROIs in the CT value data memory 25.

On the other hand, the control unit 11 updates the final high-dose X-ray scan image data already stored in the image data storage area of the display data memory 26 to the first image data obtained by the second low-dose X-ray scanning. ROI information already set is attached intact to the image data obtained by the second low-dose X-ray scanning and stored.

Furthermore, the control unit 11 supplies the CT value calculated by the CT value calculating unit 23 to the TDC data storage area of the display data memory 26 and stores them adjacent to the CT value obtained with the final high-dose X-ray scan image data. Therefore, the first image obtained by the second low-dose X-ray scanning and stored in the display data memory 26 is displayed on the monitor 28 of the monitoring unit 9. In addition, CT values obtained from the first image data by the second low-dose X-ray scanning is provided as a TDC, together with the first low-dose X-ray scan image data and high-dose X-ray scan image data (step S14).

Then, after a lapse of an inter-scan interval of Δt3 since capture of the first image data by the second low-dose X-ray scanning, the second image data is collected by the second low-dose X-ray scanning. The second image data obtained by the second low-dose X-ray scanning and CT values obtained by the image data are stored in the image data memory 22 and in the CT value data memory 25 by a procedure similar to the foregoing and displayed on the monitor 28. In the generation of the image data by the second low-dose X-ray scanning, the inter-scan interval Δt3 is set larger than the inter-scan interval Δt2 in the high-dose X-ray scanning and substantially equal to the inter-scan interval Δt1 in the first low-dose X-ray scanning.

Generation of the third and subsequent image data by the second low-dose X-ray scanning at the optimum slice positions and calculation and display of CT values are similarly performed in succession at an inter-scan interval of Δt3. The obtained image data are stored in the image data memory 22 in succession. The newest image data to which ROIs are attached are displayed on the monitor 28.

The CT value calculating unit 23 also calculates the CT values within ROIs about the second low-dose X-ray scan image data stored in the image data memory 22 on the basis of the preset ROI positional information. The calculated CT values are stored in the CT value data memory 25, and the CT values are provided at the TDCs on the monitor 28.

The operator observes the TDCs of the CT values obtained from the second low-dose X-ray scan image data. If the operator has confirmed that the values are below a given threshold value, the operator enters a command for the end of the scanning from the input unit 10 (step S15). On the basis of the command signal for the end of the scanning, the control unit 11 supplies a control signal to the high-voltage generating unit 12 and stops the supply of tube current and tube voltage to the X-ray tube 13. In addition, the control unit 11 sends a stop signal to the driving control unit 4, thus stopping all mechanical operations such as rotation of the rotating portion of gantry. Thus, capture of image data by contrast enhanced dynamic CT scan is ended.

In the above description, the scanning shifts to the second low-dose X-ray scanning at the end of the high-dose X-ray scanning to facilitate capturing the features of the TDCs of the CT values. The validity of the timing of the end of the high-dose X-ray scanning can be checked with greater ease by continuing calculations of the CT values in the second low-dose X-ray scan image data and displaying them. To reduce X-ray dose to the patient 30 further, the contrast enhanced dynamic CT scan can be ended at the end of the high-dose X-ray scanning.

According to the first embodiment described so far, the operator can easily and precisely set the optimum timing of the start of the high-dose X-ray scanning from the CT values and the shape of the TDCs obtained from the first low-dose X-ray scanning. Similarly, the optimum timing of the end of the high-dose X-ray scanning can also be determined from CT values and their TDCs obtained from high-dose X-ray scan image data. Consequently, just a precise amount of image data necessary for high-dose X-ray scanning is collected. Hence, wasteful X-ray dose to the patient 30 can be reduced.

Figure 8:
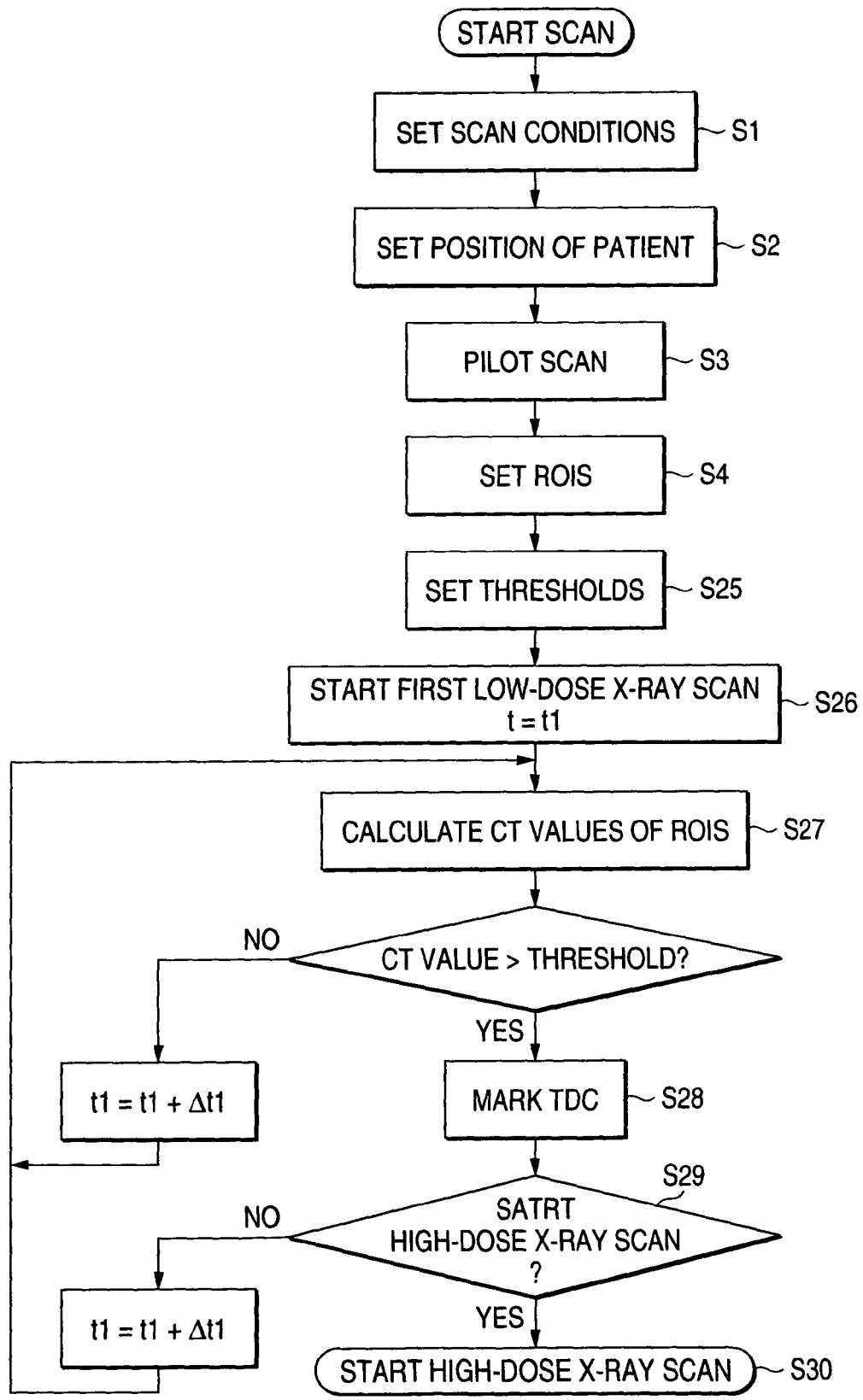
FIG. 8 is a flow chart illustrating a procedure in which contrast enhanced dynamic CT images are taken and a procedure in which CT images are displayed in a second embodiment of the present invention.
Figure 9:
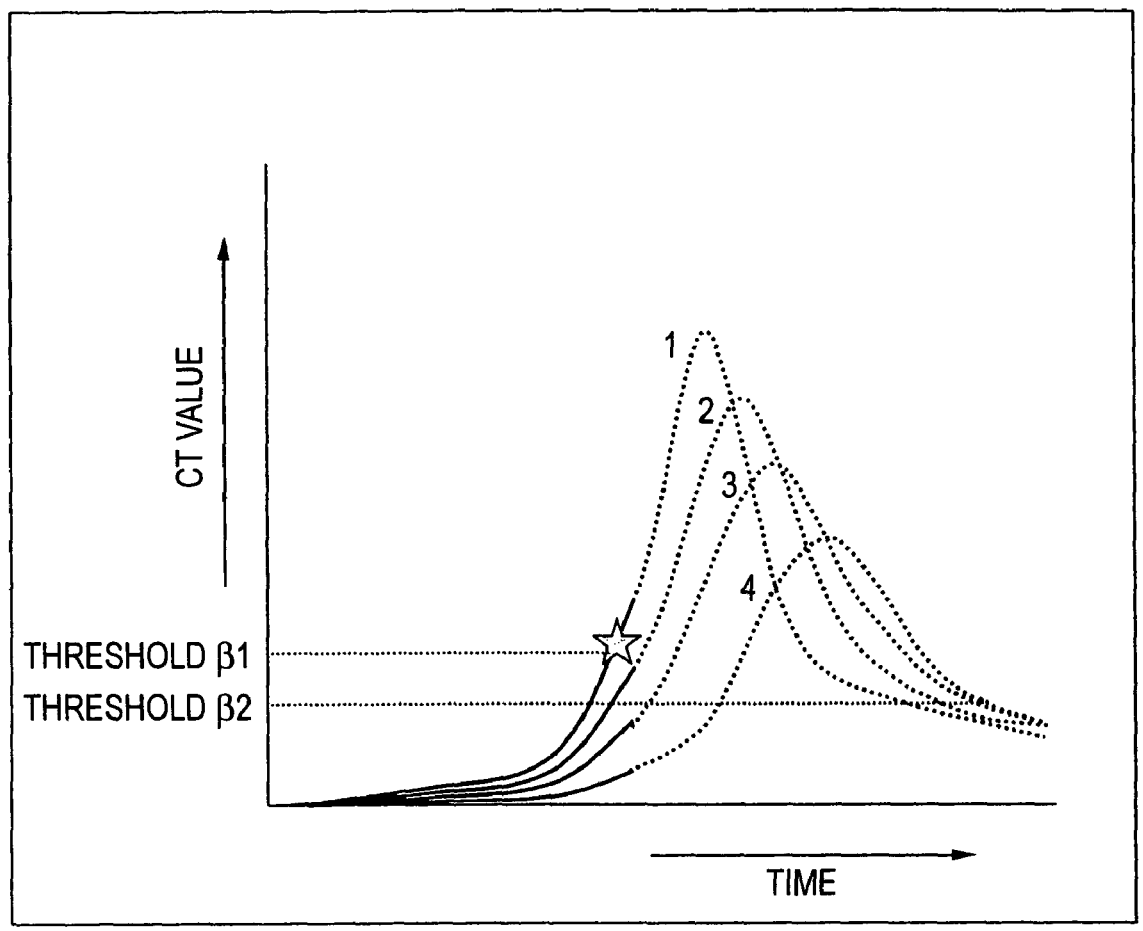
FIG. 9 is a diagram illustrating the TDCs at the end of first low-dose X-ray scanning in the second embodiment.

A second embodiment of the present invention is described using FIGS. 8 and 9.

In this second embodiment, in order to determine the timings of start and end of high-dose X-ray scanning in contrast enhanced dynamic CT, the CT values of image data are calculated by first low-dose X-ray scanning, high-dose X-ray scanning, and second low-dose X-ray scanning. The TDC of these CT values indicates that the CT values have reached a preset threshold value.

In the first embodiment already described, the operator observes the TDCs of CT values calculated in ROIs set in first low-dose X-ray scan image data and in high-dose X-ray scan image data and determines the timing of start or end of the high-dose X-ray scanning from the shape of the TDCs or the newest CT value.

In contrast, in the present embodiment, threshold values are set for the CT values, variation magnification factor of the CT values, the gradient of the TDCs indicating the shape of the TDCs, and the change of the TDC gradient with time. If the TDC reaches the threshold value during calculation of CT values, an arrival signal indicating this purport is informed to the operator. The operator determines the timing of start and the timing of end of the high-dose X-ray scanning using the TDC displayed on the monitor 28 and the arrival signal as references.

FIG. 8 illustrates a flow chart of the scanning procedure of the contrast enhanced dynamic CT in the present embodiment. In this flow chart, the same procedure as the procedure in the first embodiment described above is indicated by the same symbols and its detail description will be omitted.

The operator sets scan conditions (step S1). Then, the operator sets the position of the patient 30 (step S2). The operator captures plural images of CT image data about different slice planes through the patient 30. Image data at the slice position best adapted for contrast enhanced dynamic CT scan is selected as pilot image data from these images of CT image data (step S3). An ROI for calculations of CT values is set at a desired position in the selected pilot image data (step S4).

On completion of the ROI setting on the pilot image, the operator enters a command for setting of threshold values from the input unit 10. The control unit 11 receives the command signal and displays ROI information stored in the ROI position data memory 24 in the form of a list on the monitor 28. The operator selects the threshold value input columns which are set differently for different ROIs in the list, using the mouse of the input unit 10, and enters threshold value from the keyboard, thus ending the setting of the threshold values (step S25).

The threshold values may be set differently for different ROIs. For example, a threshold value for the start of high-dose X-ray scanning and a threshold value for the end may be set for the blood vessel (artery) at which the contrast medium arrives earliest and for the blood vessel (vein) at which the contrast medium arrives latest.

On completion of the ROI for calculations of CT values and setting of the threshold values on the pilot image, the operator injects an iodinated contrast medium into an elbow vein of the patient 30. After a lapse of a given time T0, the first low-dose X-ray scanning is started (step S26).

The driving control unit 4 rotates the rotating portion of gantry 2 and moves the couch 1 at a constant speed. The operator sets ROIs for each image data obtained by the low-dose X-ray scanning at an inter-scan interval of $\Delta t1$, on the basis of the positional information about the ROIs set previously in the pilot image data. Then, the CT values in the ROIs are calculated. Changes of CT values with time are displayed as a TDC on the monitoring unit 9 (step S27).

Where the CT value or the gradient of the TDC exceeds its given threshold value during calculation of CT values in the first low-dose X-ray scan image data, the control unit 11 marks a given position on the TDC as shown in FIG. 9 (step S28). The operator estimates the timing at which the contrast medium arrives, using the CT values. The shape of the TDC and the marks are displayed on the monitor 28 as a reference (step S29).

If the operator has recognized the optimum timing of the start of the high-dose X-ray scanning from the information about the TDC, the operator enters a command signal for starting the high-dose X-ray scanning from the input unit 10 and starts the high-dose X-ray scanning (step S30).

In the above description, the method of displaying the TDC has been described, in a case where the operator determines the timing of the start of the high-dose X-ray scanning. The timing of the end of the high-dose X-ray scanning can be determined by a similar procedure. That is, where the CT value or the gradient of the TDC reaches its given threshold value during calculation of the CT value in high-dose X-ray scan image data, the control unit 11 marks a given position of the TDC or displays a given signal on the monitoring unit 9 or on the input unit 10.

The operator determines the timing at which the contrast medium disappears (i.e., the timing at which the high-dose X-ray scanning is ended), using the mark as a reference, as well as the CT value and the shape of the TDC displayed on the monitor 28. Then, the operator enters a command signal for ending the high-dose X-ray scanning or starting the second low-dose X-ray scanning from the input unit 10, thus ending the high-dose X-ray scanning.

According to this second embodiment, a display of the TDC, which is a feature of the first embodiment. and comparative information about the preset threshold values is provided. Therefore, it is easier for the operator to determine the optimum timing of the start of high-dose X-ray scanning and optimum timing of the end of high-dose X-ray scanning.

Figure 10:
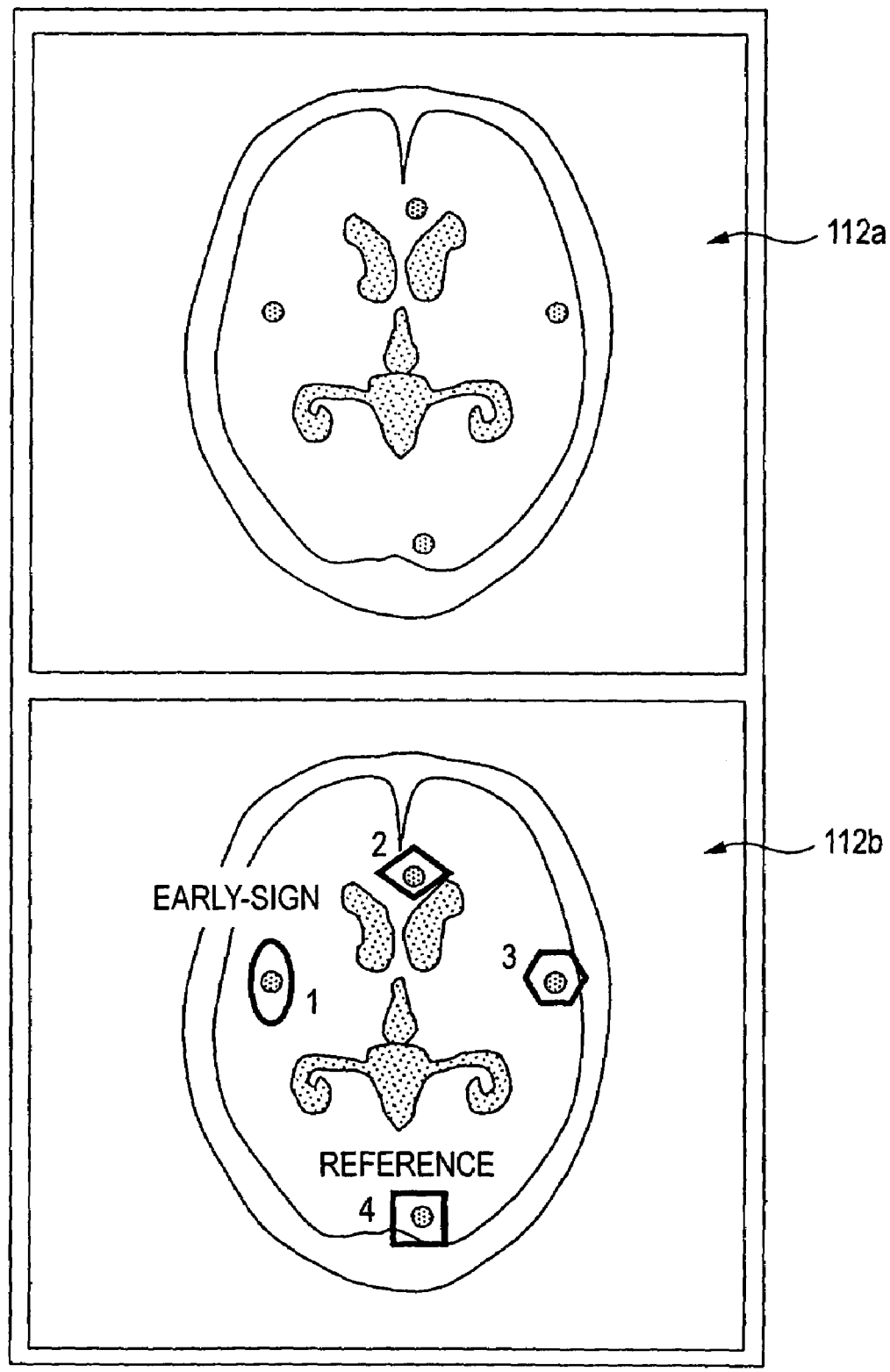
FIG. 10 is a view showing a modified example of a display of CT images in the first and second embodiments.
Figure 11:
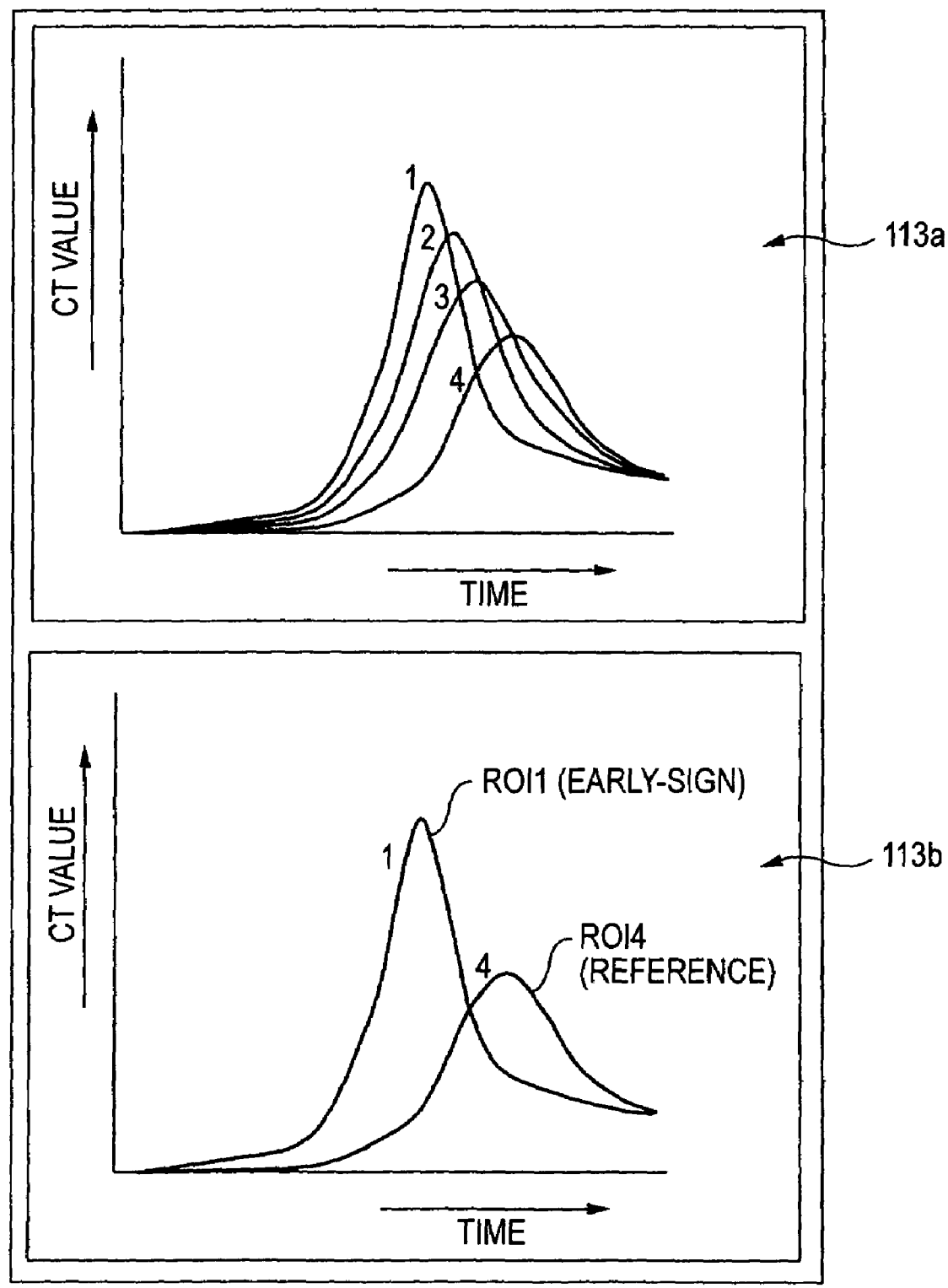
FIG. 11 is a view showing a modified example of a display of TDCs in the first and second embodiments.

While the first and second embodiments of the present invention have been described so far, the invention is not limited to the above embodiments. Rather, they can be modified in practicing them. For example, other display methods in the above embodiments are shown in FIGS. 10 and 11. FIG. 10 shows an example of display of image data. Where numerous ROIs for calculations of CT values are set on the image, boundary lines and various tags will increase in number. This makes observation of details on the image difficult. In such a case, an image 112a for diagnosis and an image 112b for setting of ROIs are separately displayed, thus solving the above-described problem.

On the other hand, FIG. 11 shows a method of displaying the TDC in a case where numerous ROIs for calculations of CT values are set. Where a number of ROIs are set, the number of TDCs increases. Especially, observation of TDCs in ROIs 1 and 4 that are important for judgment of the timings of start and end of the high-dose X-ray scanning is made difficult. An improvement can be achieved by displaying the two TDCs in ROIs 1 and 4 separately as a TDC graph 113b. At this time, the TDCs shown in the TDC graph 113b may be deleted from the TDC graph 113a.

The shape of each ROI set on a CT image is not limited to one having an area such as circle, ellipse, or rectangle. Dotted ROIs may also be possible. In the case of the dotted ROIs, however, it is desirable to sum up CT values in the surrounding pixels and take their average, for preventing the S/N deterioration.

In contrast enhanced dynamic CT, the increase in CT value may be more important in some cases than the CT value itself. In such a case, the increase in the CT value is preferably calculated and displayed as a TDC. In this case, the CT values of ROIs in the pilot image or the initial-phase image in the first low-dose X-ray scanning are used as CT values that provide a reference.

In the above-described embodiments, an iodinated contrast medium is used as a contrast medium. This contrast medium is not limited to this type. Other contrast media such as xenon-based contrast media may also be used.

Figure 12:
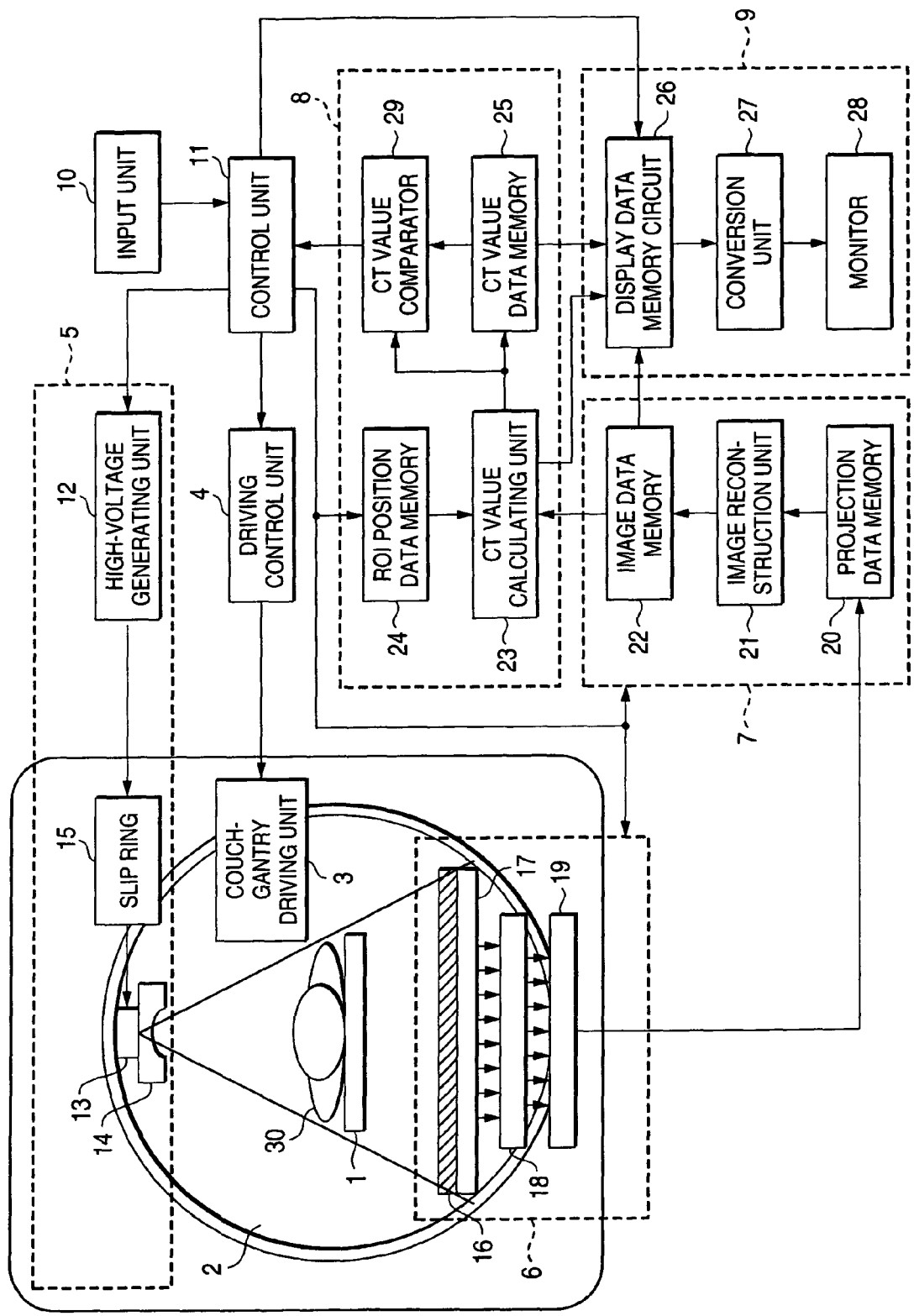
FIG. 12 is a block diagram showing the construction of an X-ray CT apparatus in a third embodiment of the present invention.
Figure 13:
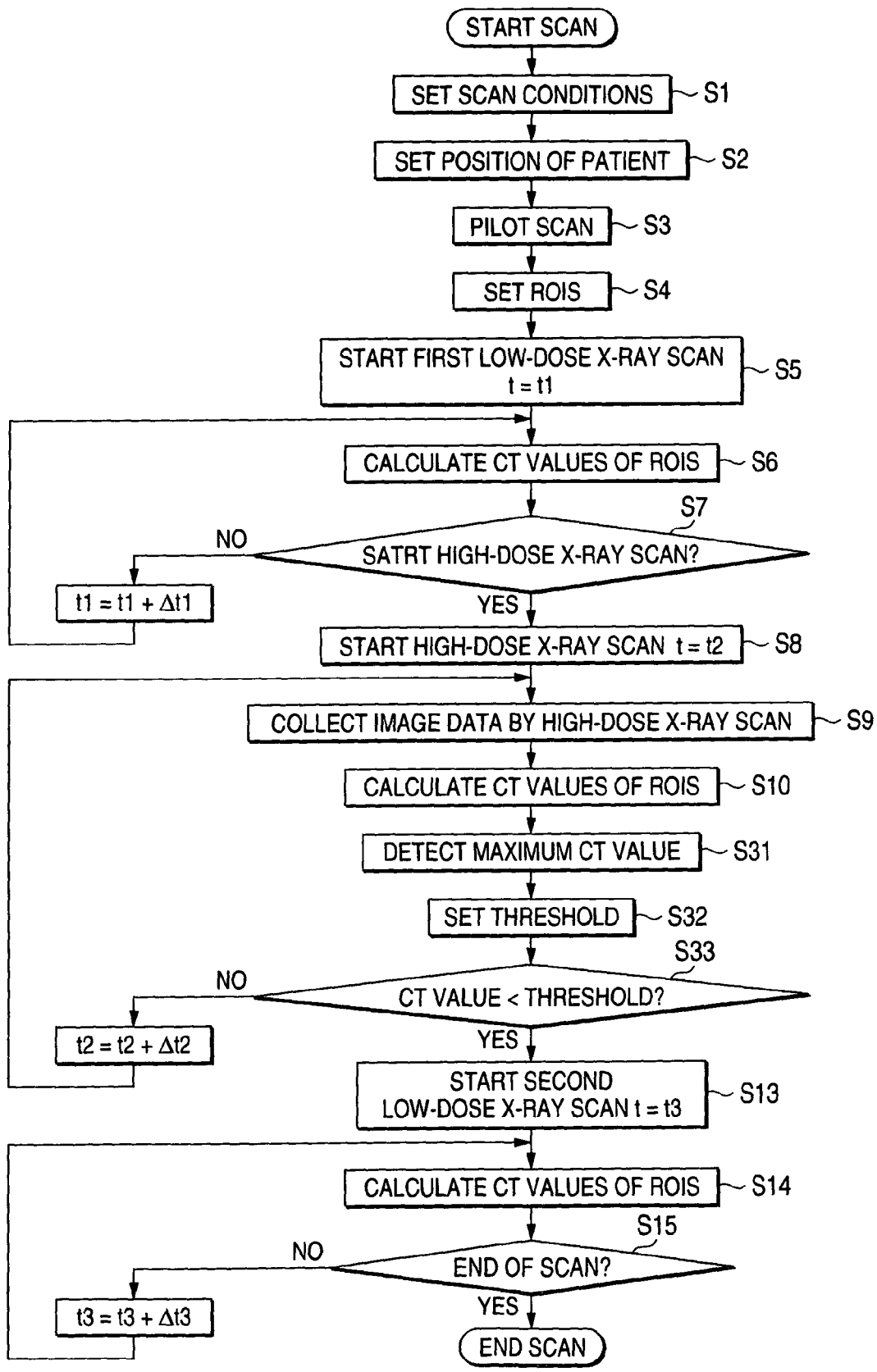
FIG. 13 is a flow chart illustrating the procedure in which contrast enhanced dynamic CT images are taken in the third embodiment.

A third embodiment of the present invention is described using FIGS. 12 and 13. In the above-described first embodiment, the second low-dose X-ray scanning is performed subsequent to the high-dose X-ray scanning to check the validity of the timing of the end of the high-dose X-ray scanning. The operator determines the end timing of the high-dose X-ray scanning from CT values and the shapes of the TDC obtained by the high-dose X-ray scan image data.

It is also possible, however, to automatically set the timing at which a switch is made from the high-dose X-ray scanning to the second low-dose X-ray scanning and the timing of the end of the second low-dose X-ray scanning. In this case, variations in the switching timings among patients are reduced by setting a given ratio (e.g., 50%) of the maximum CT value calculated during high-dose X-ray scanning as a threshold value and comparing this threshold value with CT values calculated in succession.

FIG. 12 is a block diagram showing an X-ray CT apparatus of the present embodiment. The difference with the first embodiment shown in FIG. 1 is that a CT value comparator 29 is newly added to the CT value evaluating unit 8.

This CT value comparator 29 detects the maximum CT value from CT values produced by the high-dose X-ray scanning and sets the threshold value on the basis of the maximum CT value. Furthermore, the threshold value is compared with CT values calculated by the CT value calculating unit 23 during high-dose X-ray scanning. Where the CT value decreases below the threshold value, a control signal is produced to make a switch from the high-dose X-ray scanning to the second low-dose X-ray scanning.

The procedure of capturing contrast enhanced dynamic CT images in the third embodiment of the present invention is described on the basis of the flow chart of FIG. 13. In this flow chart, the same procedure as the first embodiment shown in FIG. 3 is indicated by the same symbols and its detail description is omitted.

The operator sets scan conditions (step S1). Then, the operator sets the position of the patient 30 (step S2). The operator captures plural images of CT image data about different slice planes through the patient 30. Image data on the slice position best adapted for contrast enhanced dynamic CT scan is selected as pilot image data from these images of CT image data (step S3). ROIs for calculations of CT values are set at desired positions in the selected pilot image data (step S4).

On completion of the setting of the ROIs on the pilot image, the operator injects a contrast medium into the patient 30 and starts the first low-dose X-ray scanning (step S5).

The control unit 11 rotates the rotating portion of gantry 2 at a constant speed, and sets ROIs for CT image data successively obtained by low-dose X-ray scanning made at an inter-scan interval of $\Delta t1$. Then, the CT values in the ROIs are calculated, and the CT values are displayed as a TDC on the monitoring unit 9. (step S6).

Then, the operator observes the TDC displayed on the monitoring unit 9. The operator estimates the timing at which the contrast medium arrives from the TDC and determines the timing of the start of the high-dose X-ray scanning (step S7).

Then, the high-voltage generating unit 12 supplies tube voltage and tube current for the high-dose X-ray scanning to the X-ray tube 13 in accordance with a command signal for the start of the high-dose X-ray scanning, the signal being entered by the operator (step S8).

The X-ray tube 13 receives the supply of electric power for X-ray irradiation from the high-voltage generating unit 12 and varies the X-rays irradiation from a low-dose for the first low-dose X-ray scanning to a high-dose for the high-dose X-ray scanning. The projection data acquisition unit 6 collects X-ray projection data. The reconstruction unit 7 generates the first image data by the high-dose X-ray scanning using these projection data and stores them in the image data memory 22 (step S9).

On the other hand, the CT value calculating unit 23 reads out the first image obtained by the high-dose X-ray scanning, and CT values in ROIs on the basis of the positional information about the ROIs already stored in the ROI position data memory 24 are calculated, and the results are stored in the CT value data memory 25 (step S10).

Similarly, CT values are calculated about the second and subsequent high-dose X-ray scan data which are taken at an inter-scan interval of $\Delta t2$. And the CT values are stored in the CT value data memory 25. CT values obtained by the first low-dose X-ray scanning and high-dose X-ray scanning are displayed as TDCs on the monitor 28.

On the other hand, the CT value comparator 29 of the CT value evaluating unit 8 reads out a series of CT values calculated by the CT value calculating unit 23, and detects the maximum CT value obtained by the high-dose X-ray scanning (step S31). A threshold value is set on the basis of this maximum CT value. A value that is 50%–60% of the maximum CT value is set as this threshold value (step S32).

Then, the CT value comparator 29 compares the threshold value with the CT values in the newest image data supplied successively from the CT value calculating unit 23. Where this CT value decreases below the threshold value, the CT value comparator 29 supplies an instruction signal for switching from the high-dose X-ray scanning to the second low-dose X-ray scanning to the control unit 11 (step S33)

The control unit 11 receiving this instruction signal supplies control signals to various units and starts the second low-dose X-ray scanning (step S13). Calculations of CT values about ROIs of image data obtained by this second low-dose X-ray scanning and display of the TDCs are performed (step S14).

The operator observes the TDCs. And, if the operator confirms that it has decreased below a given threshold value, enter a command for ending of the scanning from the input unit 10 and ends the capture of contrast enhanced dynamic CT images (step S15).

According to the third embodiment described so far, when a switch is made from the high-dose X-ray scanning to the second low-dose X-ray scanning, the timing of switching is automatically set by comparing the preset threshold value with CT values obtained by the high-dose X-ray scanning. Therefore, operator's burden is alleviated.

The timing of the end of the second low-dose X-ray scanning may be automatically set by a procedure similar to the switching from the high-dose X-ray scanning to the second low-dose X-ray scanning. In this case, the operator previously sets a threshold value $\beta 3$ for determining the timing of the end of the second low-dose X-ray scanning in the same way as threshold values $\beta 1$ and $\beta 2$. When the CT value in the second low-dose X-ray scanning decreases below the threshold value $\beta 3$ the scanning is ended. Where it is difficult to set the threshold value $\beta 3$ due to a rise in the baseline of the TDC attributed by the circulation of the contrast medium through the patient 30, the difference in time ($\Delta TX$) between the time (TX1) at which the maximum CT value is obtained by the high-dose X-ray scanning and the time (TX2) at which a switch is made from the high-dose X-ray scanning to the second low-dose X-ray scanning may be measured, and the second low-dose X-ray scanning may be ended when the time $\Delta TX$ has passed from the TX2.

Where the switching timing is automatically set, the CT value or TDCs may not need to be displayed. Where the CT value decreases below a preset threshold value, a display of the timing is preferably provided on the monitoring unit 9 or on the input unit 10. In this case, the instruction signal for the switching of the scanning may be entered issued by the operator who observes the display on the monitoring unit 9 or on the input unit 10.

In the above description, the threshold value is set on the basis of the maximum CT value. It may also be a preset value or a value that is set by the operator from the input unit 10. In the latter case, the setting may be done when scan conditions are set in step S2.

Figure 14:
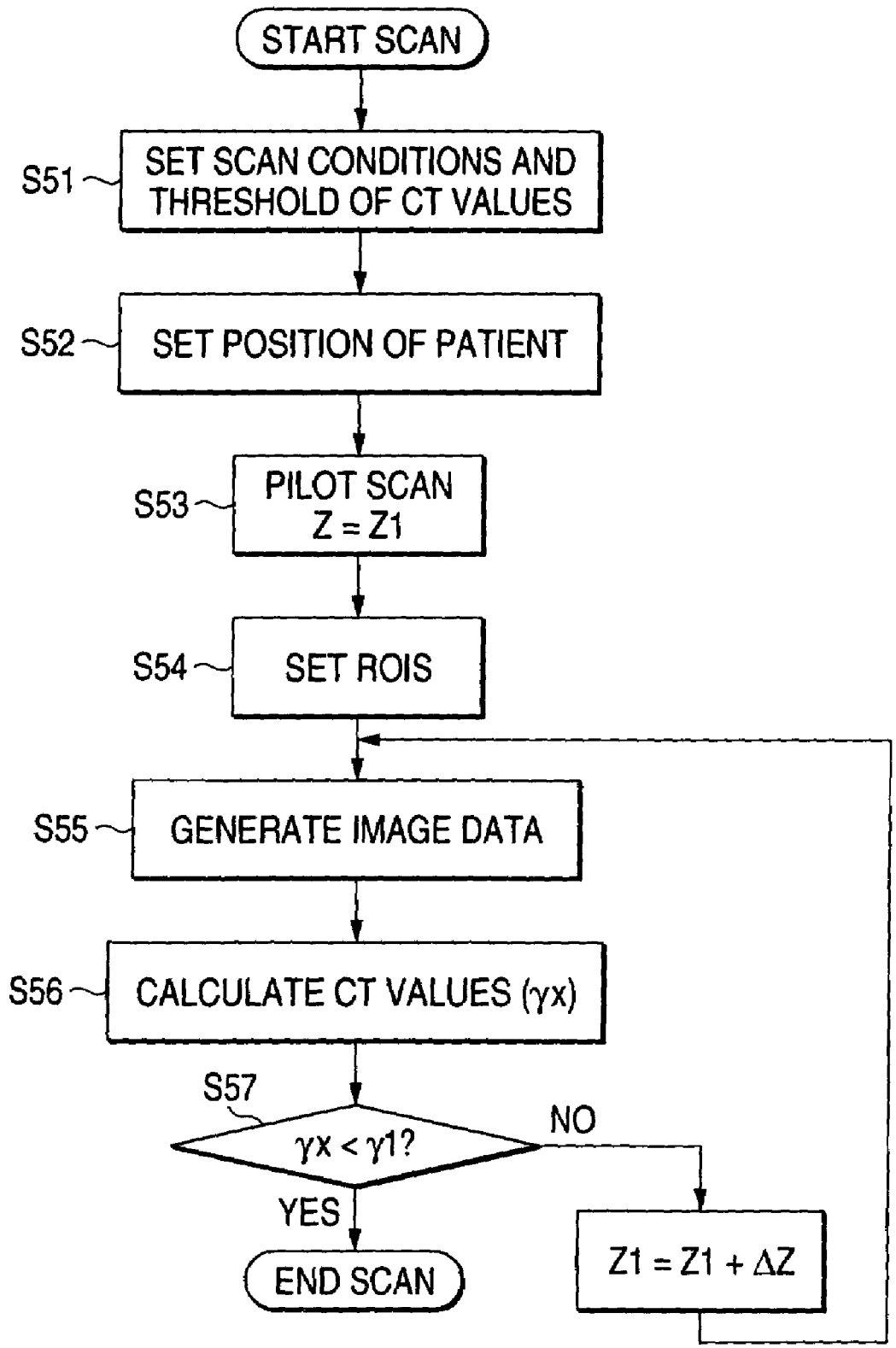
FIG. 14 is a flow chart illustrating a procedure in which CT images are taken in a fourth embodiment of the present invention.

A fourth embodiment of the present invention is described using FIGS. 12, 14, and 15. The present embodiment is an application of the first through third embodiment s and generates image data while moving slice positions. The CT values in these image data are calculated in succession. Thus, information as to whether the slice position is within the area of the patient or not is offered to the operator.

Collection of projection data, generation of image data, and setting of ROIs in the present embodiment are substantially the same as the first embodiment and so their detail description is omitted.

FIG. 14 is a flow chart illustrating the scanning procedure of the present embodiment. The operator sets various scanning conditions and threshold value $\gamma 1$ or $\gamma 2$ for CT values from the input unit 10 (step S51) in the same way as in the first embodiment. The threshold value $\gamma 1$ is a threshold value used to detect the boundary between the brain having a CT value of about 20 and the skull having a CT value of about 1000. The threshold value $\gamma 2$ is a threshold value used to detect the boundary between the skull and air having a CT value of less than −2000. A case where the threshold value $\gamma 1$ is used is described below.

The operator places the patient 30 on the top plate of the couch 1 (step S52) and moves the top plate and the patient 30 in the direction of body axis such that the area to be diagnosed such as the human head lies at a given position in the opening in the gantry. The first image data is captured as pilot image data (step S53). One or more ROIs are set for the pilot image data (step S54).

The driving control unit 4 supplies a control signal to the couch-gantry driving unit 3 according to an instruction from the control unit 11, and collects projection data about the patient 30 while moving the patient 30 at a constant speed in the direction of body axis together with the top plate of the couch 1.

Figure 15B:
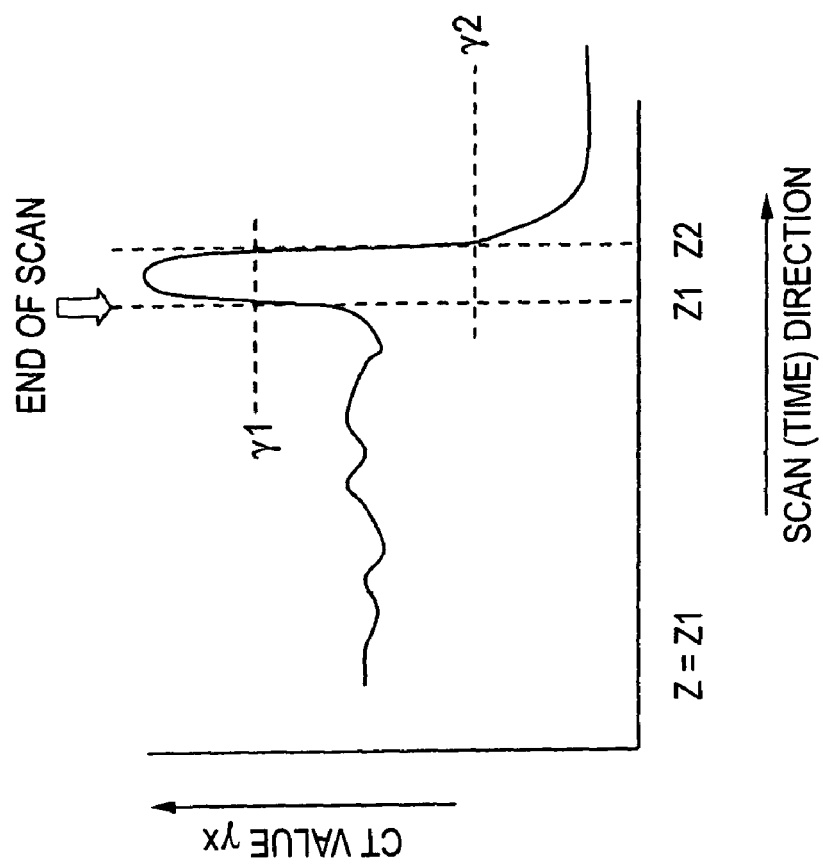
FIG. 15 is a diagram illustrating slice positions and a TDC in the fourth embodiment.
Figure 15A:
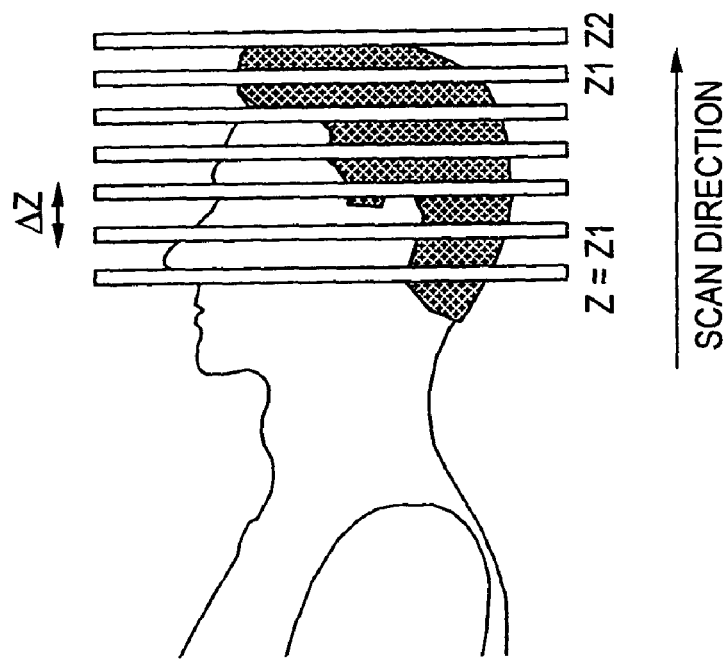

FIG. 15 shows the relation between slice positions and a TDC. FIG. 15A shows the scanned portion of the head in the present embodiment. The first image is taken at Z=Z1. A scan is made toward the vertex of the head at intervals of ΔZ to obtain create image data. Because of this scan, projection data collected at intervals of ΔZ are reconstructed, and image data are generated (step S55).

CT values γx in preset ROIs are calculated in the image data obtained, and the CT values are stored in the CT value data memory 25 and displayed as a TDC on the monitor 28 (step S56).

FIG. 15B shows the TDC displayed on the monitor 28. Where scan slice is set in the brain of the patient 30, CT values of brain tissues are obtained. As the position of scan slice moves, the CT value of the skull is calculated at Z=Z1, and the CT value of air is calculated at Z=Z2.

The CT value comparator 29 in the CT value evaluating unit 8 in FIG. 12 compares CT value γx with the threshold value γ1, where, the CT value γx being calculated at slice planes at intervals of ΔZ in the scan direction. When the CT value γx exceeds the threshold value γ1, an instruction signal for the end of the scanning is supplied to the control unit 11. The control unit 11 supplies control signals to the various units, thus ending the scanning (step S57).

In the method described above, a display of the TDC is not always necessary. Alternatively, calculated CT values or TDC may be displayed on the monitoring unit 9. The operator may observe the displayed CT values or TDC and thus determine the timing of the end of the scanning. Then, the operator may enter a command for the end of the scanning from the input unit 10. When the CT value γx and the threshold value γ1 agree, a given signal may be displayed on the monitoring unit 9 or on the input unit 10.

Preferably, the maximum value of CT values obtained in pixels, for example, in the ROIs or their average value may be used as the CT value γx used for display of the TDC.

In the above embodiment, the threshold value γ1 is selected to detect the boundary between the brain tissues and the skull. The boundary between the skull and air may be detected by selecting the threshold value γ2.

Figure 16:
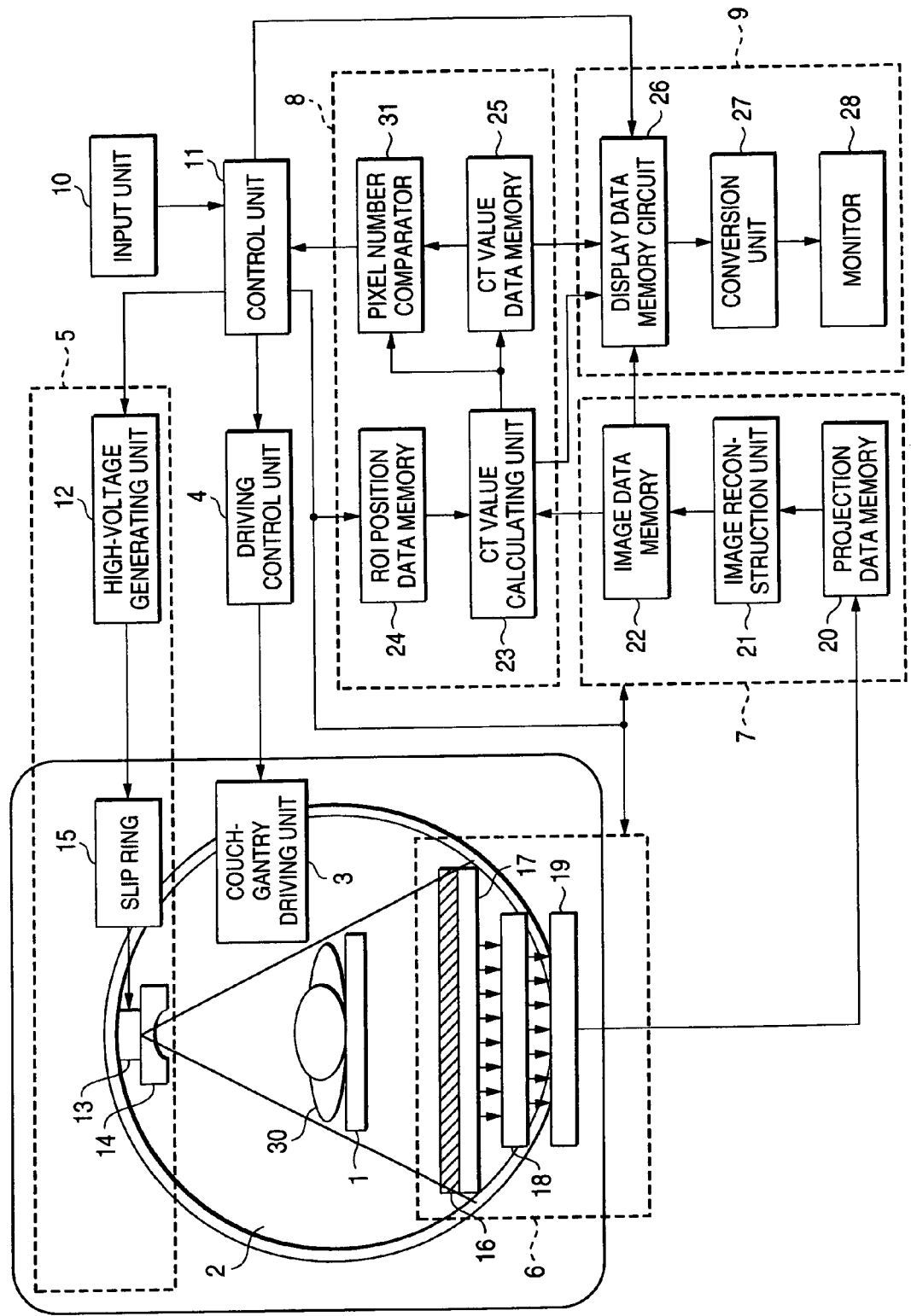
FIG. 16 is a block diagram showing the construction of an X-ray CT apparatus according to an example of modification of the fourth embodiment.
Figure 17:
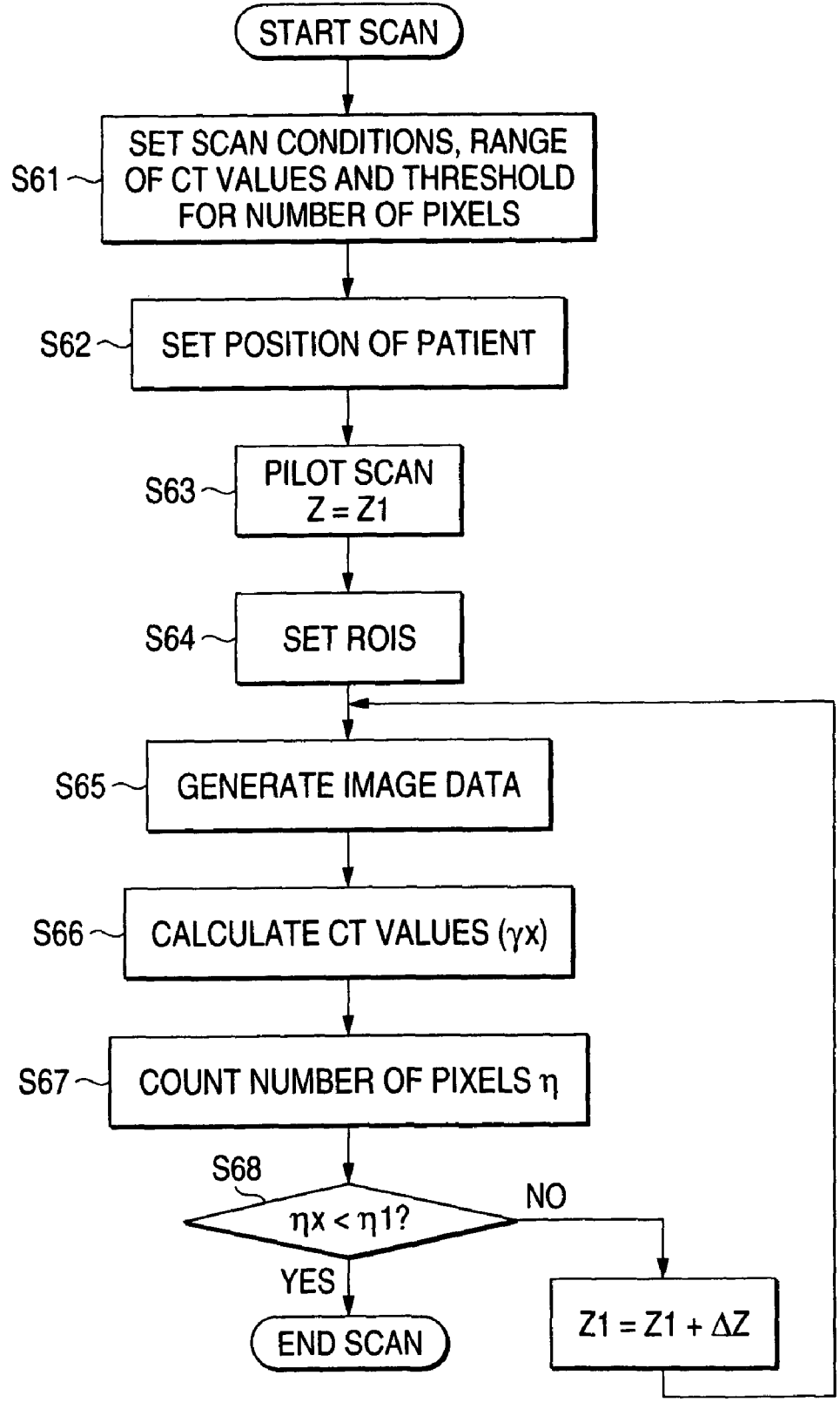
FIG. 17 is a flow chart illustrating a procedure in which CT images are taken in the example of modification of the fourth embodiment.
Figure 18A:
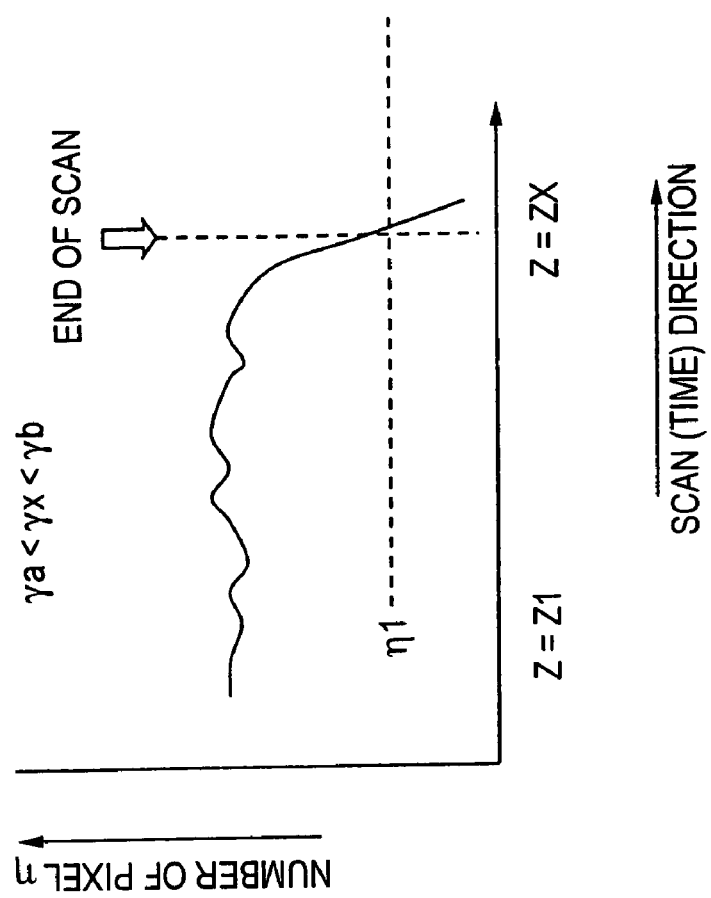
FIG. 18 is a diagram illustrating slice positions and a graph of the number of pixels in the example of modification of the fourth embodiment.

An example of modification of the fourth embodiment is described using FIGS. 16–18. In this example of modification, instead of comparison of the CT value γx with the threshold value γ1 or γ2., the timing of the end of the scanning is set by comparison of the number of pixels ηx having CT values within a given range with a threshold value η1.

FIG. 16 is a block diagram showing the configuration of an X-ray CT apparatus in the present example of modification. The difference with the first embodiment shown in FIG. 1 is that a pixel number comparator 31 is newly added to the CT value evaluating unit 8.

The CT value calculating unit 23 of the CT value evaluating unit 8 calculates the CT value γx, in pixels, in given ROIs of the image data obtained in given locations. The results of the calculations are stored in the CT value data memory 25. Meanwhile, the pixel number comparator 31 reads out the CT value γx, in pixels, stored in the CT value data memory 25 and counts the number of pixels ηx having CT values γx within a preset range of CT values, i.e., the range γa<γx<γb. The obtained number of pixels ηx is compared with a threshold value η1 for the number of pixels.

The number of pixels ηx is compared with the threshold value η1 while moving the slice position in the scan direction. An instruction signal for ending the scanning is generated when ηx<η1 is reached.

The scanning procedure of the present example of modification is described on the basis of the flow chart of FIG. 17. In this flow chart, the same procedure as the above-described fourth embodiment is indicated by the same symbols and their detail description is omitted.

In the same way as the first embodiment, the operator sets various conditions for scanning, lower limit γa and upper limit γb of the range of CT values, and the threshold value η1 for the number of pixels from the input unit 10 (step S61). The lower limit γa and upper limit γb of the range of CT values are set by adding margins to the maximum and minimum values of CT values normally calculated from the brain.

Then, the patient 30 is placed on the top plate of the couch 1. The top plate and the patient 30 are moved in the direction of body axis such that the area of the patient 30 to be diagnosed. (e.g., head) lies at a given location in the opening in the gantry (step S62). First, pilot image data is taken (step S63),and ROIs are set in this image data (step S64).

The driving control unit 4 supplies a control signal to the couch-gantry driving unit 3 and collects projection data about the patient 30 while moving the patient 30 at a constant speed in the direction of body axis together with the top plate of the couch 1.

The relation between slice positions and the TDC is shown in FIG. 18. FIG. 18 As hows scan positions through the human head in the present embodiment. The first image is obtained at Z=Z1 and a scanning is made along the scan direction at intervals of ΔZ. Because of this scan, projection data obtained at intervals of ΔZ are reconstructed, and image data are generated (step S65) Then, the CT value calculating unit 23 calculates CT values γx, in pixels, in ROIs in the image data obtained at given positions (step S66). The results of the calculations are stored in the CT value data memory 25. Meanwhile, the pixel number comparator 31 compares the CT value γx, in pixels, stored in the CT value data memory 25 with the preset range of CT values and counts the number of pixels ηx having CT values γx in the given range, i.e., γa<γx<γb, (step S67)

Figure 18B:
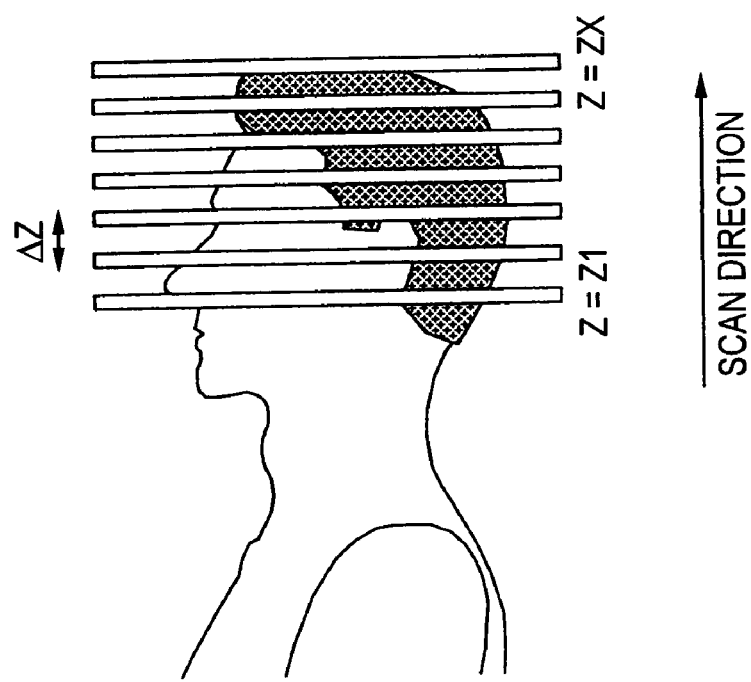

FIG. 18B shows a graph of the number of pixels ηx displayed on the monitor 28. Where the ROIs in the image data at given slice positions lie within the brain of the patient 30, the CT values γx mostly lie within the range γa<γx<γb. On the other hand, where the ROIs are outside the brain, i.e., in the skull or in air, the CT values deviate greatly from the range γa<γx<γb and so the number of pixels ηx is less than the threshold value η1.

The pixel number comparator 31 in the CT value evaluating unit 8 of FIG. 16 compares the number of pixels ηx measured in given ROIs in the slice planes set at a regular interval in the scan direction with the preset threshold value η1 (step S68), and supplies an instruction signal for ending of the scanning to the control unit 11 when ηx<η1 is reached. The control unit 11 supplies control signals to various units of the CT apparatus, thus ending the scanning.

The graph of the number of pixels shown in FIG. 18B may be displayed on the monitoring unit 9. However, this is not essential. Furthermore, the graph of the number of pixels ηx may be displayed on the monitoring unit 9, and the operator may determine the timing of the end of the scanning by observing this graph. The operator may enter a command for the end of the scanning from the input unit 10. In this case, a given signal may be displayed on the monitoring unit 9 or on the input unit 10 when the number of pixels ηx agrees with the threshold value η1.

According to the above-described fourth embodiment and its example of modification, even in normal CT scanning, the apparatus can offer the optimum timing of the end of CT scanning to the operator or automatically set the timing.

In a multi-slice system, ROIs may be set on all or some of four image data simultaneously taken at four slice positions each having a slice thickness of 1 mm, for example. Preferably, an ROI is always set in the slice closest to the vertex of the head.

While embodiments of the present invention have been described so far, the invention is not limited thereto. Rather, they may be modified in implementing them. For example, with respect to the scanning system in the above embodiments, the description centers on the multi-slice system. The invention is not limited to this system. A single slice system or helical system may also be adopted.

Furthermore, the method of determining the timing of the end of scanning from TDCs has been described. The timing may also be determined from a histogram obtained on the basis of the CT values of plural ROIs.

In addition, in the above embodiments, the first and second low-dose X-ray image data or high-dose X-ray image data on which ROIs are displayed during measurements of TDCs. It is possible not to display these image data except where ROI positions are updated.

With respect to the low-dose X-ray scanning, combined use of the method of increasing the inter-scan interval to reduce the radiation dose compared with high-dose X-ray scanning and the method of reducing the tube current has been described. Only one of them may be implemented. Additionally, the operator may detect appropriate timing from the TDC characteristics of high-dose X-ray scanning and enter an instruction signal for ending the scanning.

In the above description, the embodiments of the present invention have been described using the third generation CT apparatus. The invention is not limited to the third generation CT apparatus. The invention may also be applied to the fourth generation apparatus or CT apparatus of other generation.

Numerous and various modifications of the present invention are possible in light of the above teachings. It is therefore to be understood that, within the scope of the appended claims, the present invention can be practiced in a manner other than as specifically described herein.

What is claimed is:

1. An X-ray computer tomography apparatus comprising:
   an X-ray source configured to irradiate X-rays onto an object to be examined from plural directions;
   an X-ray detection unit configured to detect X-rays transmitted through the object;
   a driving unit configured to rotate at least one of the X-ray source and the X-ray detection unit around the object;
   a moving unit configured to move the object in a given direction;
   an image data generation unit configured to generate image data on the basis of projection data from the object collected from the X-ray detection unit plural times while moving the object by the moving unit;
   an ROI setting unit configured to set a region of interest in the image data generated by the image data generation unit;
   a CT value calculating unit configured to calculate CT values, in pixels, in the region of interest of the image data, while generating the image data by the image data generation unit;
   a range setting unit configured to set a range of the CT values;
   a pixel number measuring unit configured to measure the number of pixels providing CT values which are calculated by the CT value calculating unit and which are contained within the range set by the range setting unit;
   a threshold setting unit configured to set a threshold value for the number of pixels; and
   a pixel number comparing unit configured to keep comparing the number of pixels obtained by the pixel number measuring unit with the threshold value of the number of pixels set by the threshold setting unit and to generate an instruction signal for stopping X-ray irradiation when both substantially agree.

2. The X-ray computer tomography apparatus according to claim 1, further including a pixel number display unit, and wherein the pixel number display unit displays changes of the number of pixels with time measured by the pixel number measuring unit.

3. An X-ray computer tomography apparatus comprising:
   an X-ray source configured to irradiate X-rays into an object to be examined;
   an X-ray detection unit configured to detect X-rays transmitted through the object;
   a driving unit configured to rotate at least one of the X-ray source and the X-ray detection unit around the object;
   an image data generation unit configured to generate image data on the basis of projection data using the X-ray detection unit;
   an ROI setting unit configured to set up a region of interest in first image data from the image data generation unit, prior to injecting a contrast medium into the object;
   a CT value calculating unit configured to calculate CT values in the region of interest being set in second image data from the image data generation unit, on the basis of positional information of the region of interest, the second image data being generated plural times, after injecting the contrast medium into the object;
   a CT value display unit configured to display changes of CT values with time calculated by the CT value calculating unit;
   an irradiation condition setting unit configured to set a X-ray irradiation condition under which the X-ray source irradiates X-rays onto the object, wherein the irradiation condition setting unit modifies the X-ray irradiation condition during generation of the second image data, and to set a first irradiation condition under which low-dose X-rays are irradiated and a second irradiation condition under which high-dose X-rays are irradiated on the basis of CT values; and
   wherein the irradiation condition setting unit is further configured to set irradiation conditions for first scanning under the first irradiation condition, second scanning under the second irradiation condition, and third scanning under the first irradiation condition during generation of the second image data.

4. An X-ray computer tomography apparatus comprising:
   an X-ray source configured to irradiate X-rays into an object to be examined;
   an X-ray detection unit configured to detect X-rays transmitted through the object;
   a driving unit configured to rotate at least one of the X-ray Source and the X-ray detection unit around the object;
   an image data generation unit configured to generate image data on the basis of projection data using the X-ray detection unit;
   an ROI setting unit configured to set up a region of interest in first image data from the image data generation unit, prior to injecting a contrast medium into the object;

a CT value calculating unit configured to calculate CT values in the region of interest being set in second image data from the image data generation unit, on the basis of positional information of the region of interest, the second image data being generated plural times, after injecting the contrast medium into the object;

a threshold setting unit configured to set at least one threshold value for the CT values;

a CT value comparing unit configured to keep comparing the CT values calculated by the CT value calculating unit with the threshold value set by the threshold setting unit and to generate a coincidence signal when both substantially agree; and an irradiation condition setting unit configured to set conditions of the X-ray irradiation on the basis of an output signal from the CT value comparing unit and to set a first irradiation condition under which low-dose X-rays are irradiated and a second irradiation condition under which high-dose X-rays are irradiated, wherein the irradiation condition setting unit is further configured to set irradiation conditions for first scanning under the first irradiation condition, second scanning under the second irradiation condition, and third scanning under the first irradiation condition during generation of the second image data.

5. The X-ray computer tomography apparatus according to any one of claim 3 or claim 4, wherein the irradiation condition setting unit changes to the irradiation condition for the second scanning when a CT value in image data obtained by the first scanning has reached a first threshold value and changes to the irradiation condition for the third scanning when a CT value in image data obtained by the second scanning has reached a second threshold value.

6. An X-ray computer tomography apparatus comprising:
an X-ray source configured to irradiate X-rays onto an object to be examined;
an X-ray detection unit configured to detect X-rays transmitted through the object;
a driving unit configured to rotate at least one of the X-ray source and the X-ray detection unit around the object;
an image data generation unit configured to generate image data on the basis of projection data using the X-ray detection unit;
an ROI setting unit configured to set up a region of interest (ROI) in first image data from the image data generation unit, prior to injecting a contrast medium into the object;
a CT value calculating unit configured to calculate computer tomography (CT) values in the region of interest being set in second image data from the image data generation unit, on the basis of positional information of the region of interest, the second image data being generated plural times after injecting the contrast medium into the object; and
a CT value display unit configured to display changes of CT values with time calculated by the CT value calculating unit,
wherein the ROI setting unit further configured to attach an identifiable index to the region of interest in at least one of blood vessels at which a contrast medium arrives earliest and latest, respectively.

7. The X-ray computer tomography apparatus according to claim 6, wherein the CT value display unit configured to display changes of CT values with time in the region of interest at which a contrast medium arrives earliest and latest, in a distinguished manner from the changes of CT values with time in other regions of interest.

8. An X-ray computer tomography apparatus comprising:
an X-ray source configured to irradiate X-rays into an object to be examined;
an X-ray detection unit configured to detect X-rays transmitted through the object;
a driving unit configured to rotate at least one of the X-ray source and the X-ray detection unit around the object;
an image data generation unit configured to generate image data on the basis of projection data using the X-ray detection unit;
an ROI setting unit configured to set up a region of interest in first image data from the image data generation unit, prior to injecting a contrast medium into the object;
a CT value calculating unit configured to calculate CT values in the region of interest being set in second image data from the image data generation unit, on the basis of positional information of the region of interest, the second image data being generated plural times, after injecting the contrast medium into the object;
a threshold setting unit configured to set at least one threshold value for the CT values;
a CT value comparing unit configured to keep comparing the CT values calculated by the CT value calculating unit with the threshold value set by the threshold setting unit and to generate a coincidence signal when both substantially agree; and
an irradiation condition setting unit configured to set conditions of the X-ray irradiation on the basis of an output signal from the CT value comparing unit,
wherein the ROI setting unit is further configured to attach an identifiable index to the region of interest in at least one of blood vessels at which a contrast medium arrives earliest and latest, respectively.

9. An X-ray computer tomography apparatus, comprising:
an X-ray source configured to irradiate X-rays into an object to be examined;
an X-ray detection unit configured to detect X-rays transmitted through the object;
a moving unit configured to move the object in a given direction;
an image data generation unit configured to generate image data on the basis of projection data from the object collected from the X-ray detection unit plural times, while moving the object by the moving unit;
an ROI setting unit configured to set at least one region of interest in the image data which is obtained by the image data generation unit;
a CT value calculating unit configured to calculate CT values in the region of interest being set in the image data which is obtained by the image data generation unit, while generating the image data by the image data generation unit;
a threshold setting unit configured to set threshold values for CT values; and
a CT value comparing unit configured to keep comparing CT values obtained by the CT value calculating unit with the threshold values set by the threshold setting unit and to generate an instruction signal for stopping X-ray irradiation when both substantially agree.

* * * * *